United States Patent
Morgas et al.

(10) Patent No.: US 11,865,366 B2
(45) Date of Patent: Jan. 9, 2024

(54) STREAMLINED, GUIDED ON-COUCH ADAPTIVE WORKFLOW

(71) Applicant: SIEMENS HEALTHINEERS INTERNATIONAL AG, Steinhausen (CH)

(72) Inventors: Tomasz Morgas, Henderson, NV (US); Marco Lessard, Trois Rivieres (CA); Tobias Gass, Vogelsang AG (CH); Benjamin Haas, Brittnau (CH); Thomas Coradi, Lenzburg (CH); Jonas Honegger, Zurich (CH); Christopher Boylan, Helsinki (FI)

(73) Assignee: SIEMENS HEALTHINEERS INTERNATIONAL AG, Steinhausen (CH)

( * ) Notice: Subject to any disclaimer, the term of this patent is extended or adjusted under 35 U.S.C. 154(b) by 0 days.

(21) Appl. No.: 18/095,094

(22) Filed: Jan. 10, 2023

(65) Prior Publication Data

US 2023/0158335 A1 May 25, 2023

Related U.S. Application Data

(63) Continuation of application No. 17/471,281, filed on Sep. 10, 2021, now Pat. No. 11,583,700, which is a (Continued)

(51) Int. Cl.
*A61B 34/10* (2016.01)
*A61N 5/10* (2006.01)
(Continued)

(52) U.S. Cl.
CPC .......... *A61N 5/1039* (2013.01); *A61B 5/4836* (2013.01); *A61B 6/5247* (2013.01);
(Continued)

(58) Field of Classification Search
CPC .... A61N 5/1039; A61B 34/10; A61B 5/4836; A61B 6/5247; A61B 8/483; G16H 20/40; G16H 30/40; G06T 7/0012
See application file for complete search history.

(56) References Cited

U.S. PATENT DOCUMENTS

| | | |
|---|---|---|
| 7,020,844 B2 | 3/2006 | Trevino et al. |
| 8,019,042 B2 | 9/2011 | Shukla et al. |

(Continued)

FOREIGN PATENT DOCUMENTS

| | | |
|---|---|---|
| CN | 101268476 A | 9/2008 |
| CN | 104117151 A | 10/2014 |

(Continued)

OTHER PUBLICATIONS

Rastgarpour et al., "Application of AI Techniques in Medical Image Segmentation and Novel Categorization of Available Methods and Tools," Proceedings of the International MultiConference of Engineers and Computer Scientists, Mar. 2011, Hong Kong, vol. I.

(Continued)

*Primary Examiner* — David P Porta
*Assistant Examiner* — Fani Polyzos Boosalis
(74) *Attorney, Agent, or Firm* — Potomac Law Group, PLLC

(57) ABSTRACT

Systems and methods for implementing an adaptive therapy workflow that minimizes time needed to create a session patient model, select an appropriate plan for the treatment session, and treat the patient.

20 Claims, 18 Drawing Sheets

Related U.S. Application Data continuation of application No. 17/016,994, filed on Sep. 10, 2020, now Pat. No. 11,135,448, which is a continuation of application No. 16/233,360, filed on Dec. 27, 2018, now Pat. No. 10,799,716.

(60) Provisional application No. 62/747,439, filed on Oct. 18, 2018.

(51) Int. Cl.
*G16H 20/40* (2018.01)
*A61B 5/00* (2006.01)
*A61B 6/00* (2006.01)
*G16H 30/40* (2018.01)
*A61B 8/08* (2006.01)
*G06T 7/00* (2017.01)

(52) U.S. Cl.
CPC ............. *A61B 34/10* (2016.02); *G16H 20/40* (2018.01); *A61B 8/483* (2013.01); *G06T 7/0012* (2013.01); *G16H 30/40* (2018.01)

(56) References Cited

U.S. PATENT DOCUMENTS

| | | | |
|---|---|---|---|
| 8,144,833 | B2 | 3/2012 | Breedveld |
| 8,175,892 | B2 | 5/2012 | Kapoor et al. |
| 8,509,383 | B2 | 8/2013 | Lu et al. |
| 9,192,786 | B2 | 11/2015 | Yan et al. |
| 9,764,162 | B1 | 9/2017 | Willcut et al. |
| 9,773,219 | B2 | 9/2017 | Sankaran et al. |
| 10,025,479 | B2 | 7/2018 | Zhao et al. |
| 10,029,121 | B2 | 7/2018 | Li et al. |
| 10,049,093 | B2 | 8/2018 | Grady et al. |
| 10,549,118 | B2 * | 2/2020 | Marash ................ A61N 5/1049 |
| 11,179,129 | B2 * | 11/2021 | Harrington .......... A61B 6/5217 |
| 2006/0078086 | A1 | 4/2006 | Riley et al. |
| 2013/0326405 | A1 | 12/2013 | Nord et al. |
| 2015/0043801 | A1 | 2/2015 | Altman et al. |
| 2015/0095051 | A1 | 4/2015 | Bharat et al. |

FOREIGN PATENT DOCUMENTS

| | | |
|---|---|---|
| CN | 107072624 A | 8/2017 |
| CN | 107548497 A | 1/2018 |
| WO | WO 2010/018476 A2 | 2/2010 |
| WO | WO 2015/019215 A1 | 2/2015 |
| WO | WO 2015/038832 A1 | 3/2015 |
| WO | WO 2016/144915 A1 | 9/2016 |
| WO | WO 2017/156419 A1 | 9/2017 |

OTHER PUBLICATIONS

Schwartz et al. "Adaptive Radiation Therapy for Head and Neck Cancer-Can an Old Goal Evolve into a New Standard?" Journal of Oncology, Aug. 2010.

Extended European Search Report and European Search Opinion dated Feb. 28, 2020, in European Patent Application No. 19203518.6.

European Examination Report dated Feb. 26, 2021, in European Patent Application No. 19203518.6.

Office Action dated Dec. 16, 2022, in European Patent Application No. 19203518.6.

Office Action dated Sep. 22, 2022, in Chinese Patent Application No. 201910989664.8.

Wang et al. "Dosimetric comparison of different treatment plans in adaptive radiotherapy for head and neck cancer", Chinese Journal of Medical Physics, vol. 33, No. 10, Oct. 2016.

* cited by examiner

STREAMLINED, GUIDED ON-COUCH ADAPTIVE WORKFLOW

FIELD

The present disclosure relates generally to adaptive radiation therapy, and more particularly, to systems, methods, and devices for generating a streamlined, guided on-couch adaptive workflow for building a session patient model and selecting a treatment option in time sensitive treatment sessions.

BACKGROUND

Radiation therapy involves medical procedures that use external radiation beams to treat pathological anatomies (tumors, lesions, vascular malformations, nerve disorders, etc.) by delivering prescribed doses of radiation (X-rays, gamma rays, electrons, protons, and/or ions) to the pathological anatomy, while minimizing radiation exposure to the surrounding tissue and critical anatomical structures.

In general, radiation therapy treatments consist of several phases. First, a precise three-dimensional (3D) map of the anatomical structures in the area of interest (head, body, etc.) is constructed using any one of (or combinations thereof) a computed tomography (CT), cone-beam CBCT, magnetic resonance imaging (MRI), positron emission tomography (PET), 3D rotational angiography (3DRA), or ultrasound techniques. This determines the exact coordinates of the target within the anatomical structure, namely, locates the tumor or abnormality within the body and defines its exact shape and size. Second, a motion path for the radiation beam is computed to deliver a dose distribution that the radiation oncologist finds acceptable, considering a variety of medical constraints. During this phase, a team of specialists develop a treatment plan using special computer software to optimally irradiate the tumor and minimize dose to the surrounding normal tissue by designing beams of radiation to converge on the target area from different angles and planes. Third, the radiation treatment plan is executed. During this phase, the radiation dose is delivered to the patient according to the prescribed treatment plan. Generally, a treatment plan is delivered to the patient over a series of radiation treatments referred to as fractions.

There are many factors that can contribute to differences between the prescribed radiation dose distribution and the actual dose delivered (i.e., the actual dose delivered to the target during the radiation treatment). One such factor is uncertainty in the patient's position in the radiation therapy system. Other factors involve uncertainty that is introduced by changes that can occur during the patient's treatment. Such changes can include random errors, such as small differences in a patient's setup position. Other sources are attributable to physiological changes that might occur if a patient's tumor regresses or if the patient loses weight during therapy. Another category of uncertainty includes motion. Motion can potentially overlap with either of the categories as some motion might be more random and unpredictable, whereas other motion can be more regular.

These anatomical and physiological changes can cause the target volumes and surrounding anatomical structures and organs to move and change in size and shape during the therapy. As such, continuing to follow the initial treatment plan may result in an actual received dose distribution that differs from the planned distribution, and thus reduced doses to target volumes and/or increased doses to organs at risk (OARs). Adapting the treatment plan, namely, making modifications to the initial treatment plan to match the new location and shape of the target volume and surrounding anatomical structures based on subsequently acquired image data is one way to rectify this issue.

Adaptive radiation therapy is a process by which, using subsequent images, an original treatment plan can be adjusted to counteract these anatomical changes. The adaptive radiation therapy process is a closed-loop radiation treatment process where the treatment plan can be modified using a systematic feedback of measurements. By systematically monitoring treatment variations and by incorporating them to re-optimize the treatment plan during the course of treatment, the adaptive radiation therapy improves radiation treatment.

Adaptive radiation therapy can occur at three different timescales, namely, off-line between treatment fractions, on-line immediately prior to a treatment fraction, and in real-time during a treatment fraction.

In an off-line adaptive therapy process, during each treatment fraction, a new image (CT or CTBC image, for example) of the patient is acquired before or after each of the fractions and the images are evaluated to determine multi-day locations of the target volumes. Based on this, a new plan can be developed to better reflect the range of motion of the target volumes. Off-line adaptive processes are suitable for treating head and neck tumors, for example, where the changes are generally gradual, predictable, and slow.

In an on-line adaptive therapy process, the radiation therapy system can be used prior to a fraction to validate or adjust the patient treatment plan for the treatment delivery. The imaging system can thus be used to concurrently modify the treatment delivery to reflect the changes in the patient's anatomy. On-line adaptive processes are suitable for treating tumors located in the pelvic and upper abdominal regions where organ motions are stochastic, and changes are large, fast occurring and unpredictable, or for treating tumors in thoracic region where the changes are generally abrupt and persistent.

In a real-time (on-couch) adaptive therapy process, the radiation therapy system can be used during a treatment fraction. On-couch adaptive radiation therapy allows adjustment of treatment plan based on tumor and anatomical changes while the patient is on the treatment table. On-couch adaptive processes are suitable for treating lung tumors for example, where the changes are abrupt and persistent as well as pelvis/abdominal tumors where the changes are generally large and unpredictable. Its application, however, is limited to most needing patients due to time, workload burden and expertise required to perform on-couch adaptive radiation therapy.

Adaptive radiation therapy can also allow for recalculating the delivered dose after each fraction and accumulate these doses utilizing image deformation techniques during the accumulation to account for internal motions. The calculated doses can then be compared to the planned dose, and if any discrepancies are noted, subsequent fractions can be modified to account for the changes.

As the impact of anatomical changes and/or patient positioning depends on the individual patient and the details of the treatment plan, no general rules are applied to indicate when re-imaging and re-planning is to be done. Instead, in-treatment imaging is reviewed one or multiple times during a treatment regimen by medical personnel to verify reproducibility of patient positioning and assess anatomical changes to determine if re-planning is necessary. Subsequently, the initial treatment plan is copied onto the new image, and the dosimetric changes are assessed. If these dosimetric changes show that the target coverage or that OAR sparing may be compromised, the relevant anatomical structures are re-contoured, and a new treatment plan is created.

An exemplary workflow for adaptive radiation therapy is shown in FIG. 18. As shown in FIG. 18, after the initial set-up of the patient in the radiation treatment device (Patient Setup), a treatment session image is taken of the patient for plan adaptation (Imaging), followed by the generating of a patient session model that includes the contouring of the OARs and the target structure of interest (i.e., target volume) on the treatment session image. The contouring (segmentation, delineation) can be done manually or automatically. Manual segmentation, however, is not only time consuming, but also requires specialized knowledge as well as an expert (i.e., physician) to be present to do it. As such, using manual segmentation is not beneficial for real-time (on-couch) adaptive therapy.

On the other hand, automatically generated contours are prone to errors and uncertainties because both the target volumes and OAR structures are segmented in one step using a general-purpose algorithm. As such, these contours need to be further reviewed and edited by an expert, which adds not only additional time to the workflow but also requires the presence of an expert. Moreover, since the revision of the generated contours does not eliminate the errors that were present in the deformation (i.e., in the deformation vector field DVF), these errors will propagate to the electron density map calculated using the deformation vector field (DVF), which also adds time and need for an expert to manually correct the errors in the density map.

Furthermore, in the current planning selection process (Planning and Evaluation) it is the expert who evaluates and chooses the proper plan normalization parameters and makes plan parameter modifications which is selected on per case basis, and thus not only that it requires that an expert be present, but also increases the risk that the wrong criteria will be selected. Moreover, in current workflows, the final plan is further evaluated and approved by the expert before it can be applied for treatment delivery, which again increases the time and expertise required. In current adaptive workflows thee is also a time and computation penalty if the scheduled plan is not selected.

Thus, in current adaptive workflows, on-line adaptive planning takes a long time due to the fact that at several steps in the adaptive planning process an expert (i.e., physician) needs to be present to generate, evaluate, edit, and correct the results at each step involved in the re-planning process, since many of the currently applied processes are either not automated or they include uncertainties that either give rise to errors or propagate existing errors.

There is thus a need for an adaptive planning workflow that allows for adapting a treatment plan to the anatomy of the patient at every fraction while the patient is on the treatment couch that is fast, accurate, and limits the need for an expert/physician to be present during the treatment re-planning.

SUMMARY

Embodiments of the disclosed subject matter enable on-couch adaptive therapy workflows which minimize time needed to confidently create a session patient model, select an appropriate treatment plan for the treatment session, and treat the patient.

Embodiments of the disclosed subject matter enable creation of a workflow that is guided by prescribed adaptive directives provided by the departmental information system.

Embodiments of the disclosed subject matter enable the creation of a workflow where the quantitative criteria for plan adaptation are selected by the prescriber and automatically provided by the departmental information system to the on-couch adaptive system.

Embodiments of the disclosed workflow integrates plan checks which minimizes time spent on ensuring safety of the selected plan.

In disclosed embodiments, the treatment session patient model is built in a step wise fashion, starting from the most variable anatomy. This allows to build user confidence and provide a better starting point for subsequent segmentation algorithms, increasing chances of successful automatic generation of other structures.

In disclosed embodiments, an automated workflow for an adaptive therapy session is provided, comprising: obtaining a set of directives, the set of directives including data representing a planned treatment for a patient; and using the set of directives to perform a series of automated steps to: generate a session patient model in a step-wise fashion; generate a first and a second treatment plan for the session patient model; and select a treatment plan that is appropriate for a current treatment session.

In exemplary embodiments, the generating of the session patient model in a step-wise fashion includes: a first step wherein a treatment session image of a portion of the patient is generated, the treatment session image containing an anatomy of interest and optionally a bone structure of interest; an optional second step wherein the treatment session image is evaluated using a reference image from the set of directives, the reference image containing a corresponding reference bone structure, the treatment session image being accepted when the bone structure of interest in the treatment session image matches the bone structure in the reference image; a third step wherein, upon acceptance of the treatment session image, one or more influencer structures from the list of influencer structures are generated on the treatment session image; a fourth step wherein the generated influencer structures are evaluated based on one or more directives of the set of directives; a fifth step wherein, upon acceptance of the generated influencer structures, one or more target volumes from the reference patient model are propagated to the treatment session image; and a sixth step wherein the propagated one or more target volumes are evaluated based on one or more directives of the set of directives. Upon acceptance of the propagated target volumes, the treatment session image including the influencer structures and the propagated target volumes is accepted as the session patient model. Alternatively, the second step is performed after the target volume evaluation step.

In disclosed embodiments, the treatment isocenter can be automatically determined and, using the control points of the reference plan which can be automatically transferred and the treatment session patient model, a so-called Scheduled Plan can be generated. Using the knowledge acquired during the initial planning (provided by the departmental information system, for example), a new plan, namely, an Adapted Plan, can be automatically optimized. As result, the user is presented with two plans for a current treatment session: Scheduled Plan and Adapted Plan.

In disclosed embodiments, the plans are presented in a comparison view allowing the user to always chose the plan appropriate for the session anatomy without the need for additional computation and user manipulation of patient data.

In disclosed embodiments, a method for selecting, by a user, a treatment plan to be applied in a treatment session in an automated adaptive radiotherapy is described, the method comprising the following steps: generating a treatment session image; generating a target volume in the treatment session image; determining, by the user, whether to accept the generated target volume; generating a first treatment plan based on treatment isocenter information obtained by automatically aligning of the accepted generated target volume in the treatment session image with a corresponding reference target volume in a reference image; generating a second treatment plan based on the accepted target volume and a set of automatically generated and automatically selected optimization parameters; and determining, by the user, which treatment plan to use.

In exemplary embodiments, the optimization parameters are automatically generated using previously set clinical goals.

In exemplary embodiments, the optimization parameters are continuously modified and automatically selected without the user's input.

In exemplary embodiments, the generating of the first treatment plan includes: determining a reference treatment isocenter location for the reference image; determining an acquisition isocenter location for the treatment session image; automatically aligning the accepted generated target volume in the treatment session image with the corresponding reference target volume in the reference image; determining difference between location of the reference treatment isocenter and the acquisition isocenter; determining treatment session isocenter location by applying the determined difference to the acquisition isocenter location; and using the treatment session isocenter location as input to a plan generation algorithm to generate the second treatment plan.

In exemplary embodiments, the generating of the second treatment plan includes using an optimization parameter optimized plan generation algorithm to generate a plan and optimizing the generated plan using information contained in a reference treatment plan associated with the reference target volume.

In exemplary embodiments, the generating of the target volume in the treatment session image includes automatically propagating the reference target volume from the reference image to the treatment session image using structure-guided deformable registration. The structure-guided deformable registration can be a deformable registration that is guided by one or more structures that are present in the reference image and the treatment session image. The one or more structures in the treatment session image can be generated by one of a manual, automatic, or a combination of manual and automatic delineations, and/or by propagating the one or more structures from the reference image by deformable and/or rigid deformations. The one or more structures include anatomical structures that influence one of a shape, size, or location of the target volume, and/or non-volumetric structures.

In exemplary embodiments, the method further comprises verifying, by the user, that the one or more structures are acceptable prior to being used to guide the propagation of the reference target volume to the treatment session image.

In disclosed embodiments, the determining whether to accept the generated target volume includes: presenting the reference image including the reference target volume and the treatment session image including the generated target volume to the user for comparison; and the user verifying that the generated target volume in the treatment session image represents a same anatomical region as the reference target volume in the reference image.

An adaptive therapy workflow for generating a session patient model and selecting a treatment plan for the treatment session is also disclosed, the workflow, comprising: obtaining a set of directives, the directives including information relating to a planned treatment of a patient; using the set of directives to guide the adaptive workflow to generate a session patient model in a step-wise fashion starting with the most variable anatomy; using directives from the set of directives to continuously and automatically optimize a treatment plan generated for the session model thereby obtaining an adapted plan for the treatment session; using the generated session model to automatically transfer control points of the planned treatment thereby generating a scheduled plan for the treatment session; and using directives from the set of directives to allow a user to select the treatment plan appropriate for the treatment session.

A system configured to perform the method steps as disclosed herein is also disclosed.

A system including a computer processing device configured to execute a sequence of programmed instructions embodied on a computer-readable storage medium, the execution thereof causing the system to execute the method steps disclosed herein is also disclosed.

A non-transitory computer-readable storage medium upon which is embodied a sequence of programmed instructions for the generation of day to day treatment images to be used in adaptive radiation therapy, and a computer processing system that executes the sequence of programmed instructions embodied on the computer-readable storage medium are also disclosed. Execution of the sequence of programmed instructions can cause the computer processing system to execute the adaptive workflow described herein.

Objects and advantages of embodiments of the disclosed subject matter will become apparent from the following description when considered in conjunction with the accompanying drawings.

DETAILED DESCRIPTION

Figure 1:
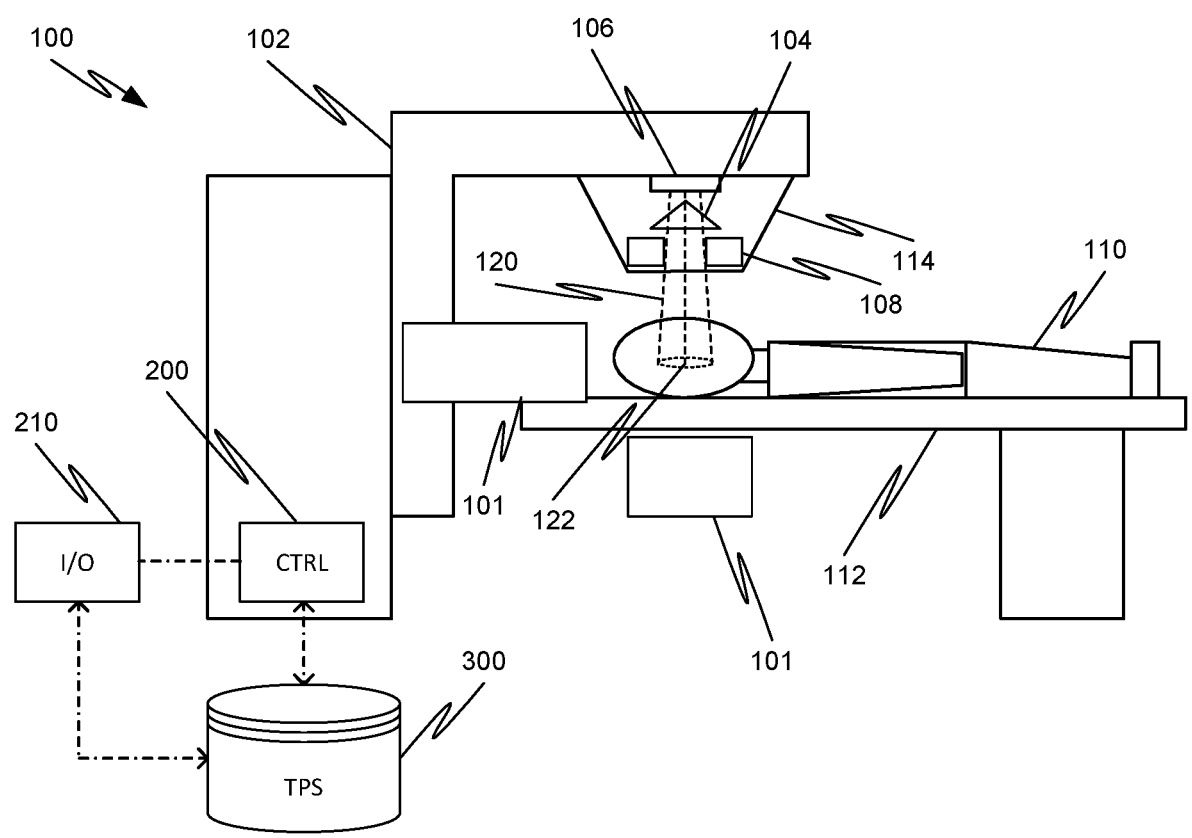
FIG. 1 is a simplified schematic diagram of a radiation therapy system, according to various embodiments of the disclosed subject matter.
Figure 2:
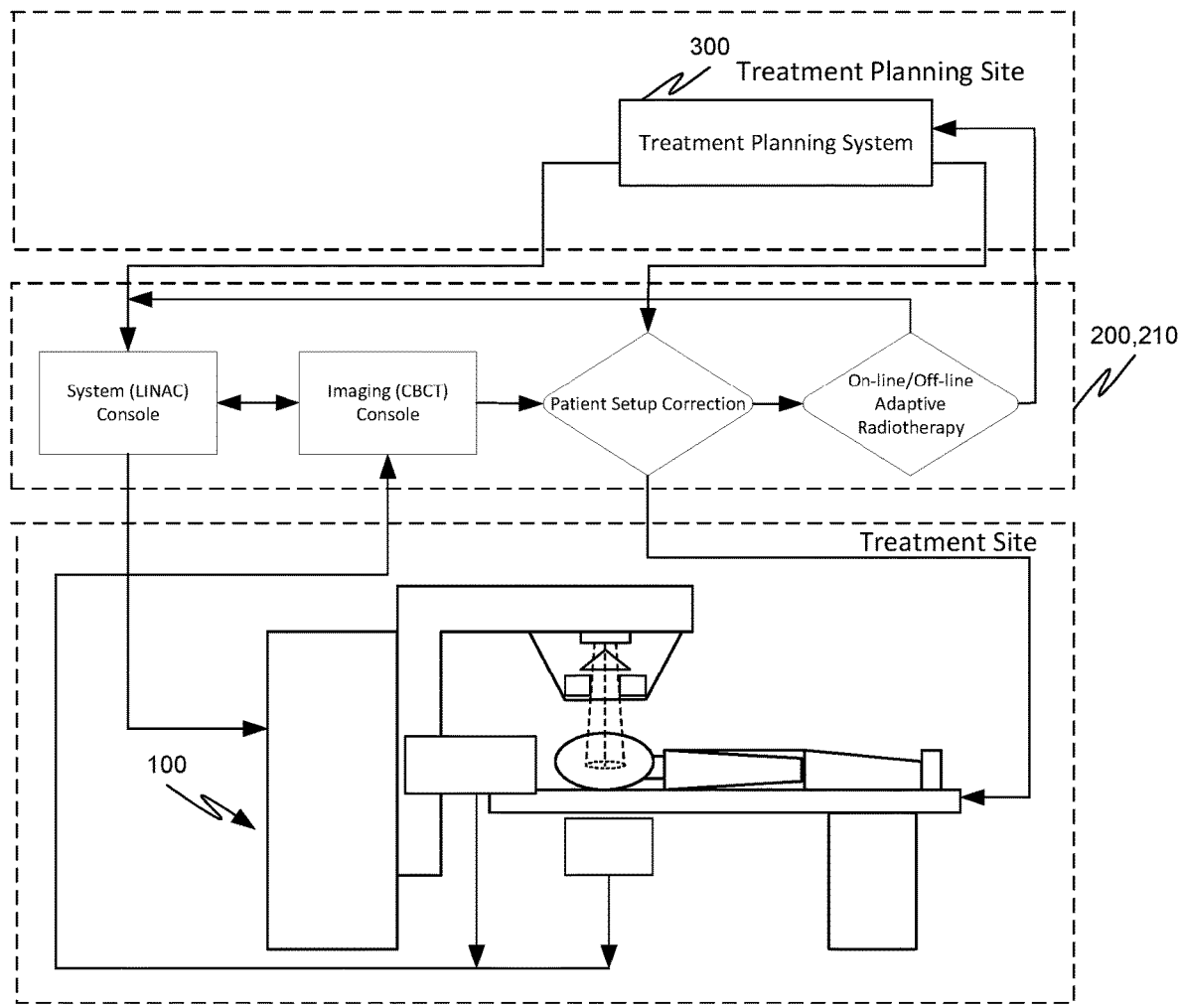
FIG. 2 is a simplified illustration for using the radiation therapy system of FIG. 1 for on-couch adaptive radiation therapy, according to various embodiments of the disclosed subject matter.

Referring to FIG. 1, an exemplary radiation therapy system 100 is shown that can be used in adaptive radiation therapy as shown in FIG. 2. The radiation therapy system 100 can provide radiation to a patient 110 positioned on a treatment couch 112 and can allow for the implementation of various radiation dose verification protocols. The radiation therapy can include photon-based radiation therapy, particle therapy, electron beam therapy, or any other type of treatment therapy.

In an embodiment, the radiation therapy system 100 can include a radiation treatment device 101 such as, but not limited to, a LINAC operable to generate one or more beams of megavolt (MV) X-ray radiation for treatment. The LINAC may also be operable to generate one or more beams of kilovolt (kV) X-ray radiation, for example, for patient imaging. The system 100 has a gantry 102 supporting a radiation treatment head 114 with one or more radiation sources 106 and various beam modulation elements, such as, but not limited to, flattening filter 104 and collimating components 108. The collimating components 108 can include, for example, a multi-leaf collimator (MLC), upper and lower jaws, and/or other collimating elements. The collimating components 108 and/or the flattening filter 104 can be positioned within the radiation beam path by respective actuators (not shown), which can be controlled by controller 116.

The gantry 102 can be a ring gantry (i.e., it extends through a full 360° arc to create a complete ring or circle), but other types of mounting arrangements may also be employed. For example, a static beam, or a C-type, partial ring gantry, or robotic arm can be used. Any other framework capable of positioning the treatment head 114 at various rotational and/or axial positions relative to the patient 110 may also be used.

In an embodiment, the radiation therapy device is a MV energy intensity modulated radiation therapy (IMRT) device. The intensity profiles in such a system are tailored to the treatment requirements of the individual patient. The IMRT fields are delivered with MLC 108, which can be a computer-controlled mechanical beam shaping device attached to the head 114 and includes an assembly of metal fingers or leaves. For each beam direction, the optimized intensity profile is realized by sequential delivery of various subfields with optimized shapes and weights. From one subfield to the next, the leaves may move with the radiation beam on (i.e., dynamic multi-leaf collimation (DMLC)) or with the radiation beam off (i.e., segmented multi-leaf collimation (SMLC)).

Alternatively, or additionally, the radiation therapy device 101 can be a tomotherapy device where intensity modulation is achieved with a binary collimator (not shown) which opens and closes under computer control (e.g., control 116). As the gantry 102 continuously rotates around the patient 110, the exposure time of a small width of the beam can be adjusted with opening and closing of the binary collimator, allowing radiation 120 to be directed to a portion of the body of the patient 110 and delivered to a region of interest 122 through the most desirable directions and locations of the patient 110. The region of interest is a two-dimensional area and/or a three-dimensional volume that is desired to receive the radiation and it may be referred to as a target or target region or target volume. Another type of region of interest is a region of risk. If a portion includes a region of risk, the radiation is diverted from the region of risk. The patient 110 may have more than one target region that needs to receive radiation therapy.

Alternatively, or additionally, the radiation therapy device can be a helical tomotherapy device, or a simplified intensity modulated arc therapy (SIMAT) device, a volumetric modulated arc therapy (VMAT) device, or a volumetric high-definition (or hyperarc) therapy (HDRT). In effect, any type of IMRT device can be employed as the radiation therapy device 101 of system 100, and can also include an on-board volumetric imaging, which can be used to generate in-treatment image data generated during a treatment session.

For example, embodiments of the disclosed subject matter can be applied to image-guided radiation therapy (IGRT) devices, which uses cross-sectional images of a patient's internal anatomy taken during the radiation therapy treatment session (i.e., in-treatment images) to provide information about the patient's position. Frequent two or three-dimensional imaging during the radiation treatment is used to direct the therapeutic radiation utilizing the imaging coordinates of the actual radiation treatment plan. This ensures that the patient is localized in the radiation treatment system in the same position as planned, and that the patient is properly aligned during the treatment. Although, the IGRT process involves conformal radiation treatment guided by specialized imaging tests taken during the planning phase, it does rely on the imaging modalities from the planning process as the reference coordinates for localizing the patient 110 during treatment. Thus, associated with each image-guided radiation therapy system is an imaging system to provide in-treatment (treatment session) images that are used to set-up the radiation delivery procedure.

In-treatment images can include one or more two or three-dimensional images (typically X-ray) acquired at one or more different points during treatment. There are a variety of ways to acquire in-treatment images. In certain approaches, distinct independent imaging systems and/or imaging methods are used for acquiring pre-treatment and in-treatment images, respectively. For example, a 3D IGRT could include localization of a cone-beam computed tomography (CBCT) dataset with a planning computed tomography (CT) dataset, and a 2D IGRT could include matching planar kilovoltage (kV) radiographs or megavoltage (MV) images with digital reconstructed radiographs (DRRs) obtained from the planning CT.

Another approach is to use portal imaging systems. In portal imaging systems, a detector is placed opposite the therapeutic radiation source to image the patient for setup and in-treatment images. Another approach is X-ray tomosynthesis which is an in-treatment imaging modality for use in conjunction with radiation treatment systems.

Alternatively, the system 100 can include a kilovoltage or a megavoltage detector operable to receive the radiation beam 120. The radiation therapy device 101 and the detector can operate as a computed tomography (CT) system to generate CT images of the patient. The images can illustrate the patient's body tissues, organs, bone, soft tissues, blood vessels, etc. Alternatively, the radiation therapy device can operate as an MRI device to generate images of the patient.

Each type of radiation therapy device can be accompanied by a corresponding radiation plan and radiation delivery procedure.

The controller 200, which can be, but is not limited to, a graphics processing unit (GPU), can include a computer with appropriate hardware such as a processor, and an operating system for running various software programs and/or communication applications. The controller 200 can include software programs that operate to communicate with the radiation therapy device 101, which software programs are operable to receive data from external software programs and hardware. The computer can also include any suitable input/output (I/O) devices 210, which can be adapted to allow communication between controller 200 and a user of the radiation therapy system 100, e.g., medical personnel. For example, the controller 200 can be provided with I/O interfaces, consoles, storage devices, memory, keyboard, mouse, monitor, printers, scanner, as well as a departmental information system (DIS) such as a communication and management interface (DICOM) for storing and transmitting medical imaging information and related data and enabling the integration of medical imaging devices such as scanners, servers, workstations, printers, network hardware, etc.

Alternatively, or additionally, the I/O devices 210 can provide access to a network (not shown) for transmitting data between controller 200 and remote systems. For example, the controller 200 can be networked via I/O 210 with other computers and radiation therapy systems. The radiation therapy system 100, the radiation treatment device 101, and the controller 200 can communicate with a network as well as databases and servers, for example, a dose calculation server (e.g., distributed dose calculation framework) and/or a treatment planning system 300. The controller 200 may also be configured to transfer medical image related data between different pieces of medical equipment.

The system 100 can also include a plurality of modules containing programmed instructions (e.g., as part of controller 200, or as separate modules within system 100, or integrated into other components of system 100), which instructions cause system 100 to perform different functions related to adaptive radiation therapy or other radiation treatment, as discussed herein, when executed. For example, the system 100 can include a treatment plan module operable to generate the treatment plan for the patient 110 based on a plurality of data input to the system by the medical personnel, a patient positioning module operable to position and align the patient 110 with respect to a desired location, such as the isocenter of the gantry, for a particular radiation therapy treatment, an image acquiring module operable to instruct the radiation therapy system and/or the imaging device to acquire images of the patient 110 prior to the radiation therapy treatment (i.e., pre-treatment/reference images used for treatment planning and patient positioning) and/or during the radiation therapy treatment (i.e., in-treatment session images), and to instruct the radiation therapy system 100 and/or the imaging device 101 or other imaging devices or systems to acquire images of the patient 110.

The system 100 can further include a radiation dose prediction module operable to predict a dose to be delivered to the patient 110 before commencement of the radiation treatment therapy, a dose calculation module operable to calculate the actual dose delivered to the patient 110 during radiation therapy treatment, a treatment delivery module operable to instruct the radiation therapy device 100 to deliver the treatment plan to the patient 110, a correlation module operable to correlate the planning images with the in-treatment images obtained during radiation therapy, a computation module operable to reconstruct three-dimensional target volumes from in-treatment images, an analysis module operable to compute displacement measurements, and a feedback module operable to instruct the controller in real-time to stop radiation therapy based on a comparison of the calculated displacement with a predetermined threshold value (range).

The system 100 can further include one or more contour generation modules operable to generate contours of target volumes and other structures in pre-treatment (planning, reference) and in-treatment (treatment session) images, an image registration module operable to register pre-treatment images with subsequent in-treatment images, a dose calculation module operable to calculate accumulated dose, a contour propagation module operable to propagate a contour from one image to another, a contour verification module operable to verify a generated contour, a registration deformation vector field generation module operable to determine deformation vector fields (DVFs) as a result of an image deformation process. The system 100 can further include modules for electron density map generation, isodose distribution generation, does volume histogram (DVH) generation, image synchronization, image display, treatment plan generation, treatment plan optimization, automatic optimization parameter generation, updating and selection, and adaptive directives and treatment information transfer. The modules can be written in the C or C++ programming language, for example. Computer program code for carrying out operations as described herein may be written in any programming language, for example, C or C++ programming language.

The treatment planning system 300 can be used to generate treatment plans for the radiation treatment device 101 based on image data, such as CT or CBCT image data, for example. In a typical planning process, qualified medical personnel (physician) manually draw contours on one or more of the initial reference planning images. These contours delineate the malignant tumor that is to be irradiated, as well as one or more other structures, such as organs, tissue, etc. that are susceptible to substantial damage from radiation exposure. The planning images can also be semi-automatically segmented to delineate the malignant tumor that is to be the target of the irradiation, and any surrounding critical structures (OARs) whose irradiation should be limited. Typical delineations for the malignant tumor include the gross target volume (GTV), the clinical target volume (CTV), and the planning target volume (PTV). The (GTV) determines the anatomic region which harbors the highest tumor cell density and requires the highest prescribed dose.

The (GTV) is the position and extent of the gross tumor, i.e. what can be seen, palpated or imaged. The (CTV) contains the (GTV), plus a margin for sub-clinical disease spread which therefore cannot be fully imaged. The (CTV) is very important because this volume must be adequately treated to achieve cure. The (PTV) allows for uncertainties in planning or treatment delivery. It is a geometric concept designed to ensure that the radiotherapy dose is actually delivered to the CTV. The (PTV) is thus used to compensate for treatment setup uncertainties through volumetric expansion of the (CTV) margins. The reference/planning images can also illustrate soft tissues, influencer structures, organs, blood vessels, bones, etc.

Once the physician generates a list of treatment parameters, such as but not limited to, the targets for which the radiation is to be maximized, targets for which the radiation is to be minimized, a treatment plan is generated that also takes into consideration constraints imposed on the treatment process by the radiation therapy system 100 used for delivering the radiation to the patient. Additionally, or alternatively, the treatment planning system 300 can use information from other imaging modalities, such as MRI, PET, etc., and/or other image data for generating the treatment plans. The treatment plan is then reviewed by the physician to ensure that it meets the clinical needs of the patient.

The physician also develops a set of adaptive directives which is a list of parameters/directives/information that describes the intent of the adaptive treatment, namely, the 4D description of the planned treatment for the patient. The set of adaptive directives can include information regarding the planned (reference) dose specification (i.e., Rx prescription), whether adaptive or standard IGRT therapy is to be used, the prescribed clinical goals, such as but not limited to, the target dose coverage and (OAR) risk dose limits, planned (reference) clinical goal values, the planning (reference) image, such as but not limited to a CT image, supporting images with their corresponding registration information (PET, MRI, etc.), the planned (reference) patient model (i.e., the contours of the reference structures, such as the target volumes, OARs and other structures on the reference image), the planned (reference) treatment plan (RT Plan), the planned (reference) treatment plan 3D dose (i.e., RT 3D dose), a list of the reference structures (target volumes, OARs, influencer structures, body outlines), a list of influencer structures of different treatment sites, information regarding the shapes and location of the planned (reference) structures on the planned (reference) image, as well as any information as to how the planned (reference) treatment plan was optimized.

The intent of the adaptive radiotherapy is to appropriately modify the radiation treatment plan to account for the temporal changes in the anatomy. As such, images, such as CBCT images for example, obtained during a treatment session (i.e., treatment session images) at the treatment site are sent to the treatment planning system 300 where a new treatment plan can be adapted to the current anatomy via deformable registration software and sent back to the radiation therapy system 100 for delivery. For on-couch adaptive radiotherapy, the workflow involved in such adaptive therapy has to be fast enough to be able to adapt the radiation plan to the new anatomy while the patient is still on the couch.

In order to achieve an accurate on-couch adaptive workflow, first an accurate session patient model (i.e., contours on the current anatomy) needs to be generated, then the treatment plan properly modified to fit the new anatomy, then quickly evaluated for application on the patient. The on-couch adaptive workflows described herein achieve this by generating a session patient model in a step-wise fashion through a series of automated steps guided by the set of adaptive directives previously determined by a prescriber (i.e., physician, for example) during treatment planning. The set of directives are also used to guide the generation and the selection of a treatment plan that is most appropriate for the current anatomy of the patient.

In an on-couch adaptive workflow shown in FIGS. 2-4 and 14, the set of adaptive directives developed by the prescriber, are either sent to the controller 200 to be saved therein and/or are made available during the adaptive therapy session via the departmental information system (DICOM, for example).

The reference image in the set of directives may be an image that was obtained previously, e.g., in a different imaging session, for the same or a different patient, that may have occurred on a different day, or on the same day. The reference image may also be an image of a different individual, in which case, image registration can be used to map the patient image to an atlas patient image. The reference image may also be an image that was artificially created via artificial intelligence (AI) segmentation that does not correspond to any individual.

In an exemplary embodiment, the reference image is a planning image obtained for the patient 110 during the treatment planning phase. The reference image can include a set of delineated reference structures, such as one or more target volumes (PTV, CTV, GTV, for example), one or more affected organs (OARs, for example), one or more anatomical structures of interest (body outlines, for example), as well as one or more influencer structures (organs and/or non-volumetric structures, for example).

For example, the reference image may contain a target volume including the primary tumor (i.e., primary target), the primarily affected organ (i.e., primary organ), and a region where invasion of lymph nodes has been observed or is to be expected (i.e., nodal target). Alternatively, the reference image may contain a target volume including the primary target, the primary organ, and the nodal target, and may contain one or more contours delineating other anatomical structures of interest. Alternatively, the reference image may include a plurality of target volumes. Alternatively, the reference image may contain a plurality of target volumes, with each target volume including a different type of primary and/or nodal target and/or primary organ. Alternatively, the reference image may include a plurality of target volumes and one or more primary organs and one or more other anatomical structures of interest.

The reference image can also include contours of structures that influence one or more of the shape, size, and location of one or more of the primary target, the nodal target, the primary organ, and the other anatomical structures of interest. These influencer structures can include structures, such as organs, that generally move and/or exhibit large deformations and/or movements from day to day, as well as other non-volumetric structures, such as points or 2D lines, for example, that describe an anatomical situation. The contours of these influencer structures generally do not propagate well from the planning image onto the treatment session image due to their highly deformable nature. Information regarding the shapes and locations of these reference structures in the reference image are also included in the set of adaptive directives as the reference patient model.

Figure 16:
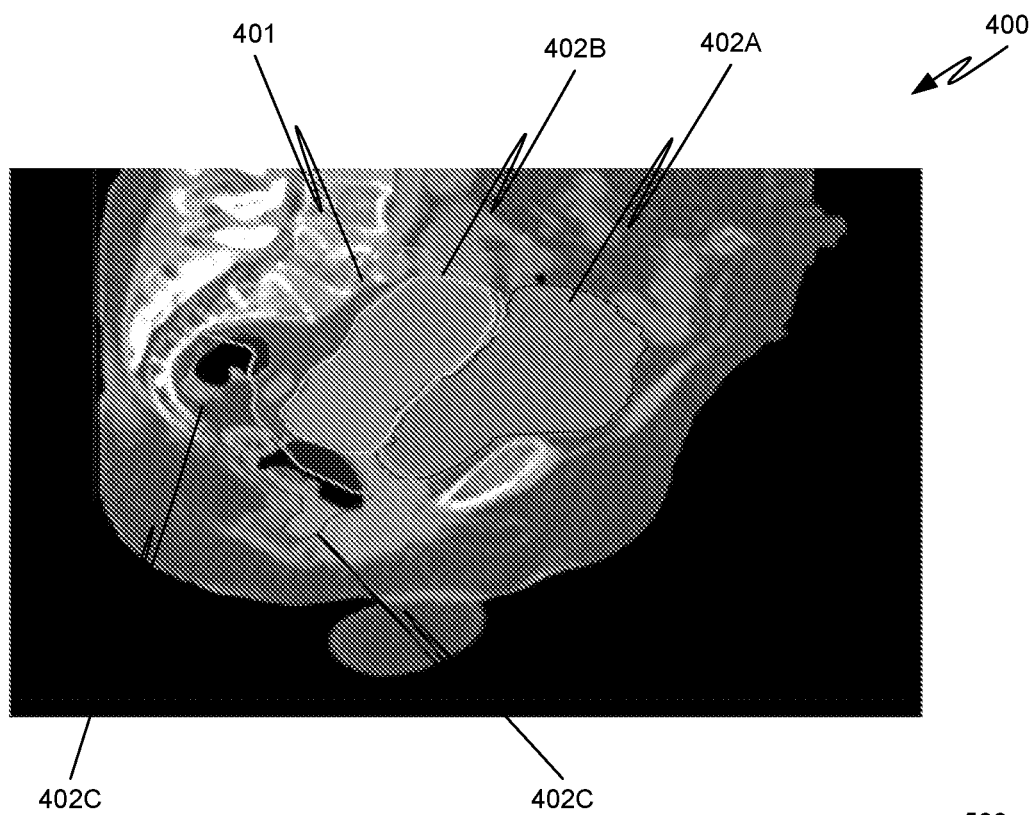
FIG. 16 is an exemplary sagittal CT slice showing a target volume and influencer structures in a female pelvis.

FIG. 16 shows an exemplary reference image 400 for a cervix uteri treatment. The reference image 400 includes a contour 401 delineating the primary and nodal targets as the target volume, and a set of contours 402, such as a contour 402A delineating the bladder, a contour 402B delineating the uterus, and contours 402C delineating the rectum, as the influencer structures. Reference image 400 may also include other structures of interest, such as body outlines or femoral heads, etc., as shown in FIG. 16.

Figure 17A:
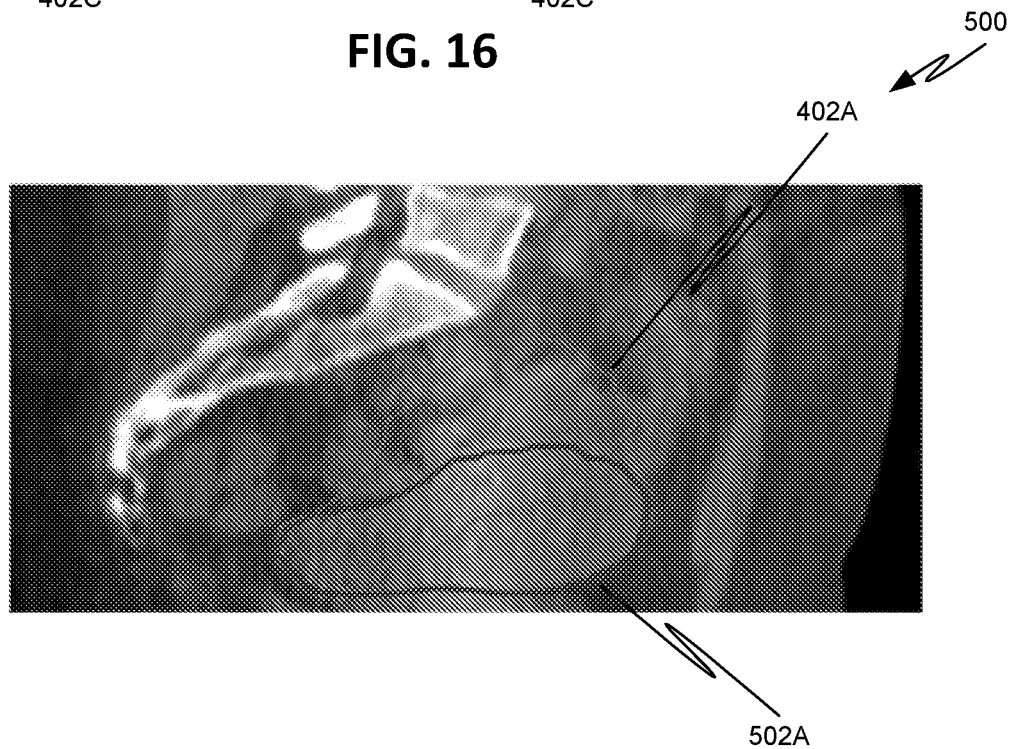
FIG. 17A is an exemplary sagittal CT slice showing a motion range of an influencer structure.
Figure 17B:
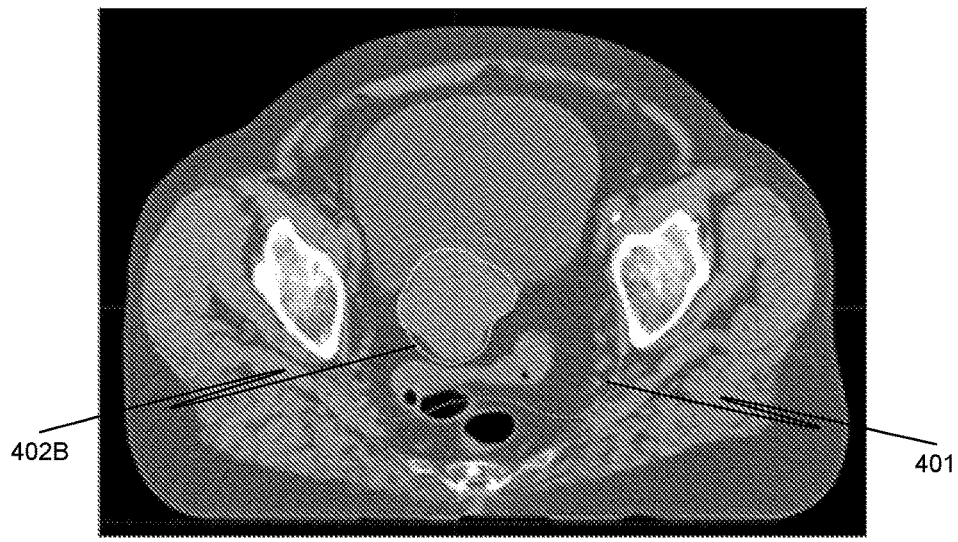
FIGS. 17B-17D are exemplary axial CT slices showing the motion range of a target volume and influencer structure.
Figure 17C:
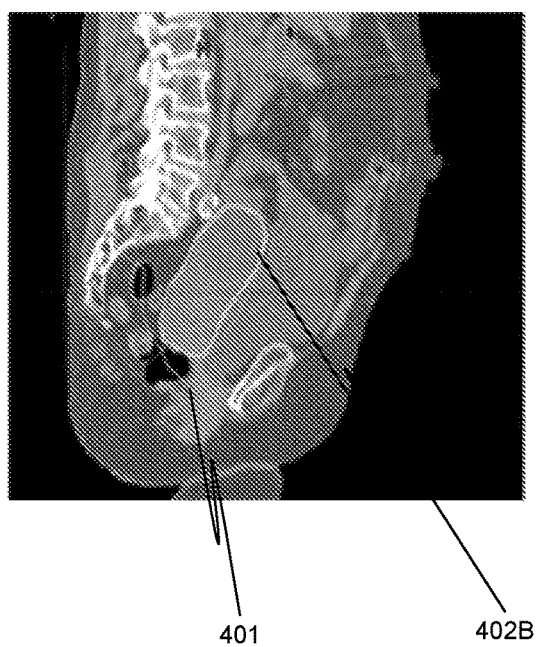
Figure 17D:
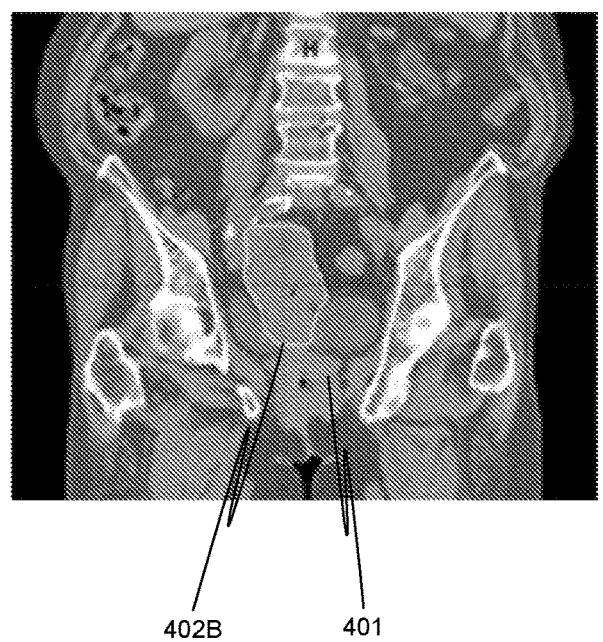
Figure 18:
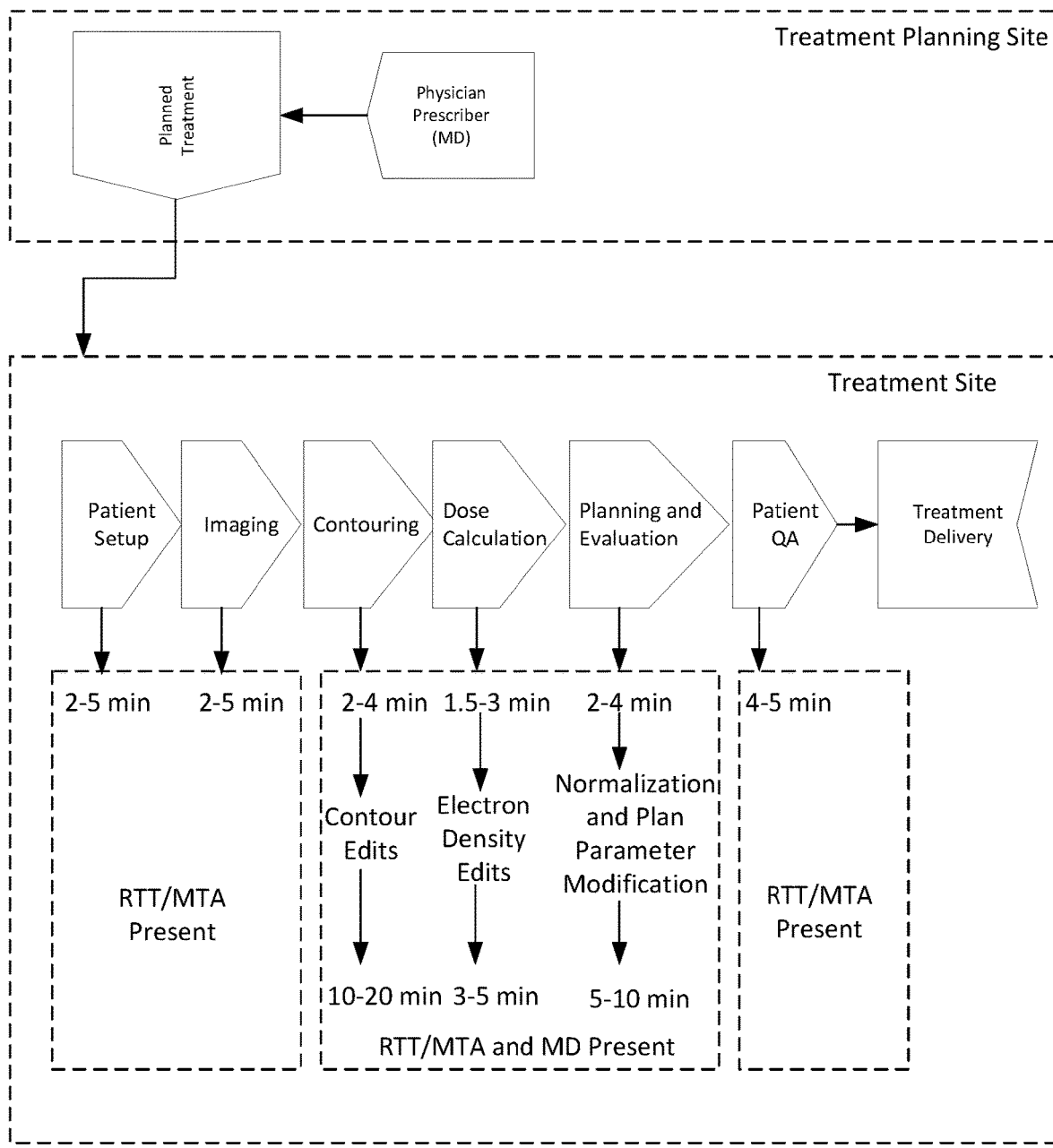
FIG. 18 is a conventional adaptive workflow diagram.

FIG. 17A shows the bladder 402A having moved from a first location (402A) to a second location (402A'), and FIGS. 17B-17D show how a target volume 401 moves from day to day due to the movement of the uterus 402B.

Although these images show specific structures used for the target volume and influencer structures, it is to be understood that the target volumes and influencer structures are not limited to these specific structures, and that any structures may be used that are relevant for a specific treatment, such as, but not limited to, the treatment of prostate, pancreas, rectal cancer, etc. Also, the influencer structures may also include structures that are non-volumetric structures, such as points or 2D lines that help describe an anatomical situation.

In order to adapt a new treatment plan to the current anatomy, once the set of adaptive directives are made available at the treatment site, a radiation technologist (RTT/MTA) who is skilled and trained at reviewing anatomy and plan selection, and who is tasked to deliver the adaptive treatment on the patient (i.e., the user/adapter), executes the first level of treatment modification, which is setting the patient on the treatment couch and moving the patient to the imaging position (Patient Setup, S102).

After the patient setup, the next step is to acquire, prior to the treatment, at the treatment site, one or more treatment session images (Imaging, S103) of the portion of the patient 110 that is of interest, using the radiation imaging device 101. In an exemplary embodiment, the treatment session image is a 3D or 4D CBCT scan for example obtained during a treatment session by irradiating the region of interest of the patient 110 with radiation 120. This treatment session image may show boney structures of the patient but does not include any delineations of target volumes or other structures.

Figure 5:
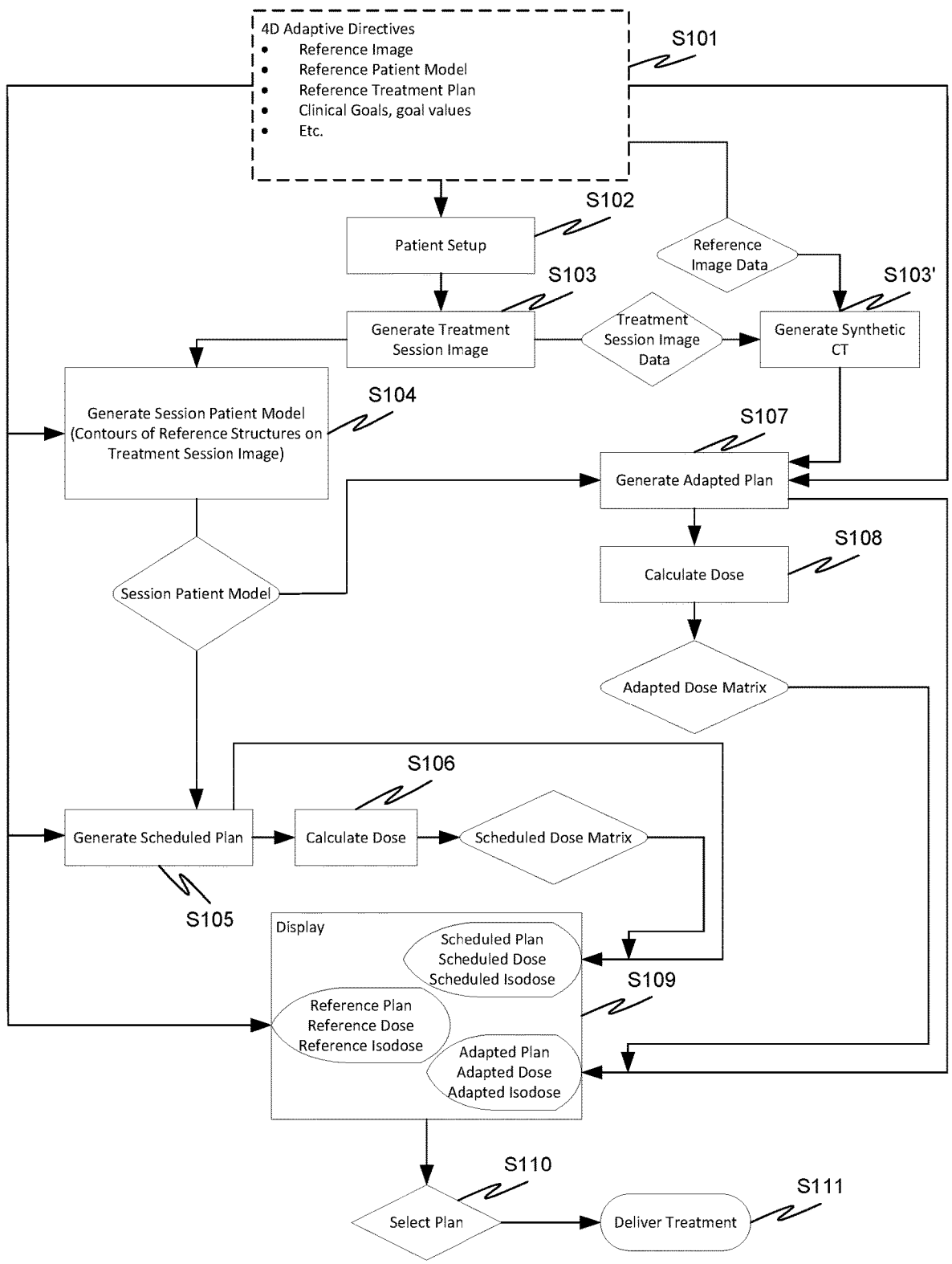
Figure 6:
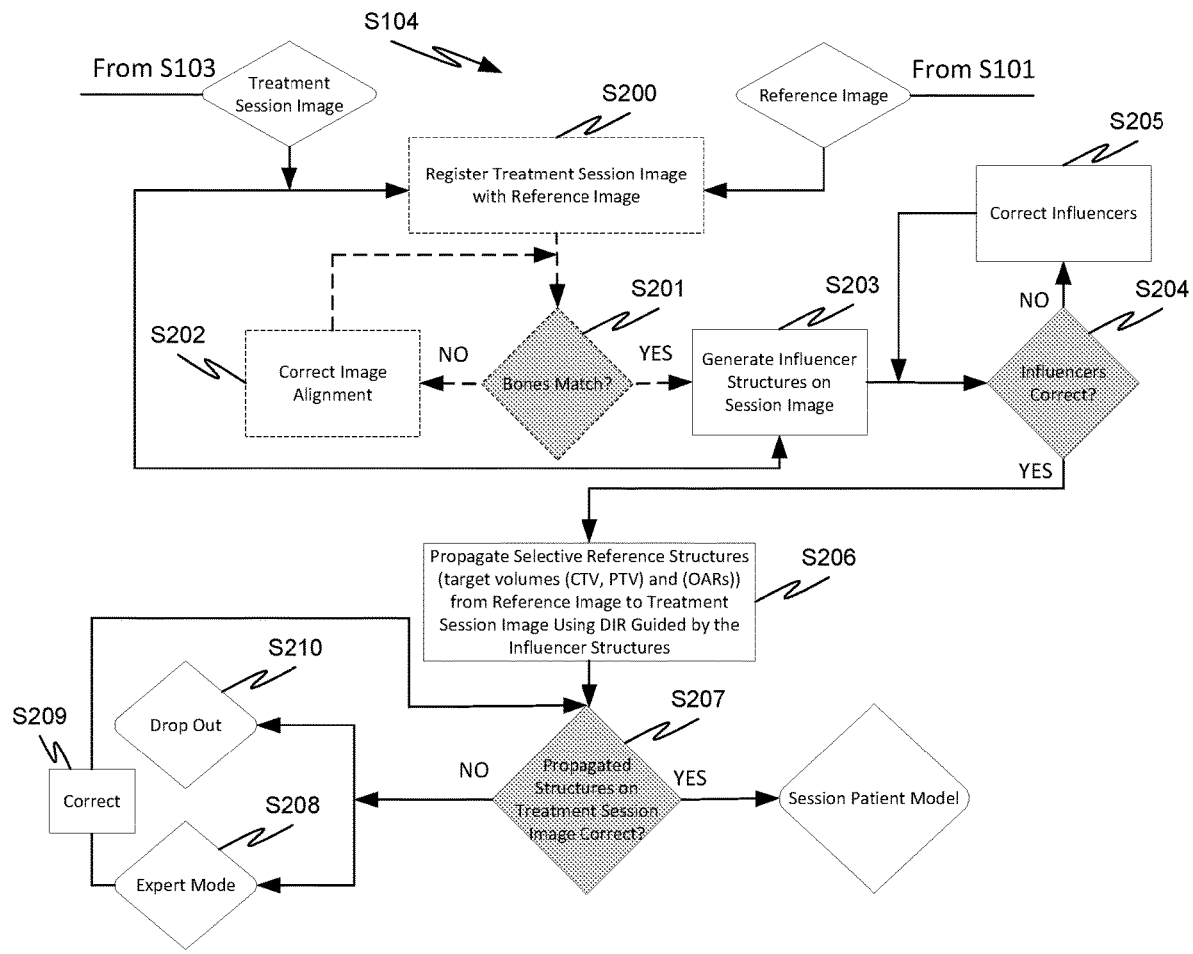
FIG. 6 is a process flow diagram for a session patient model generation, according to various embodiments of the disclosed subject matter.
Figure 7:
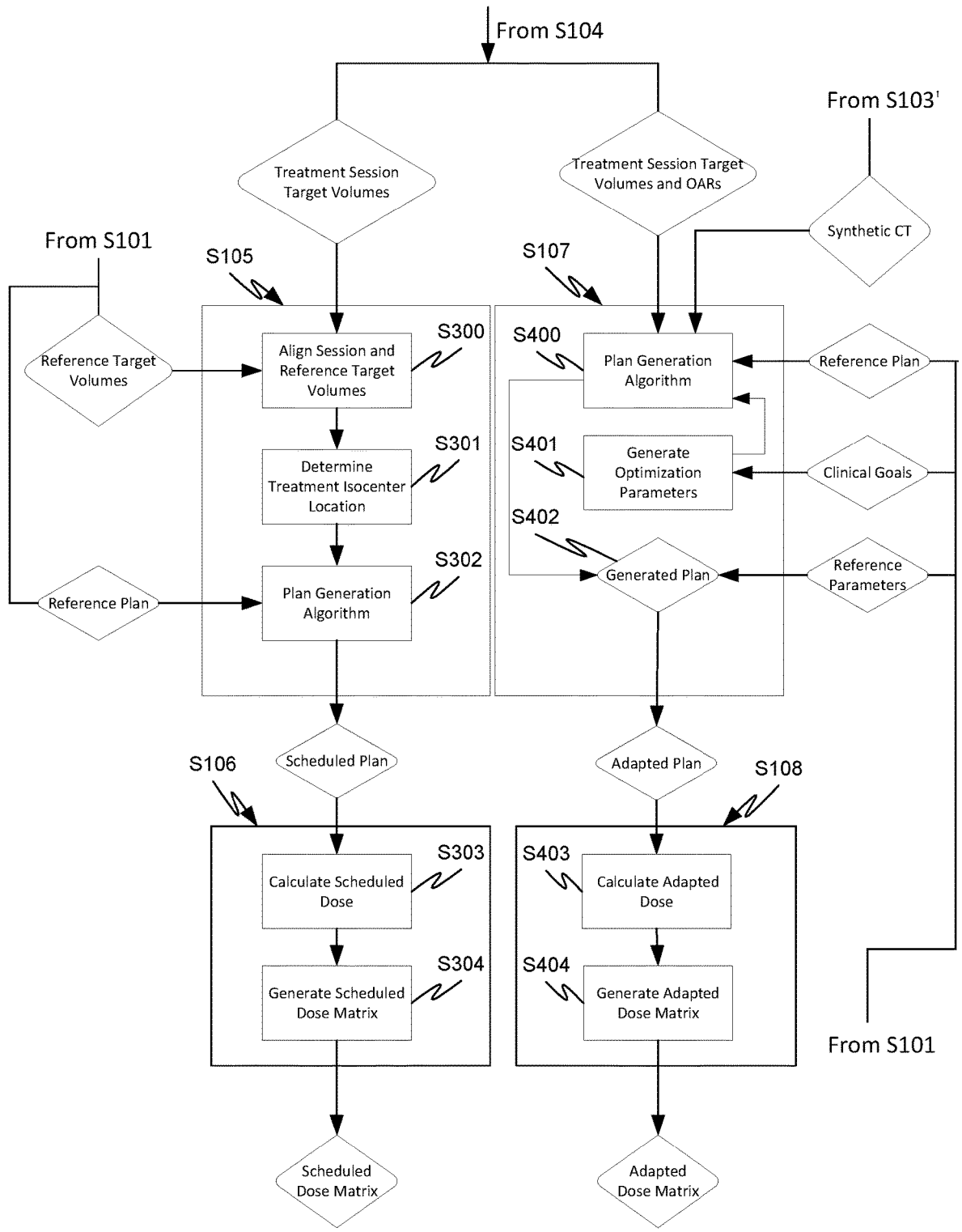
FIG. 7 is a process flow diagram for generating different treatment plans for a session patient model, according to various embodiments of the disclosed subject matter.
Figure 8:
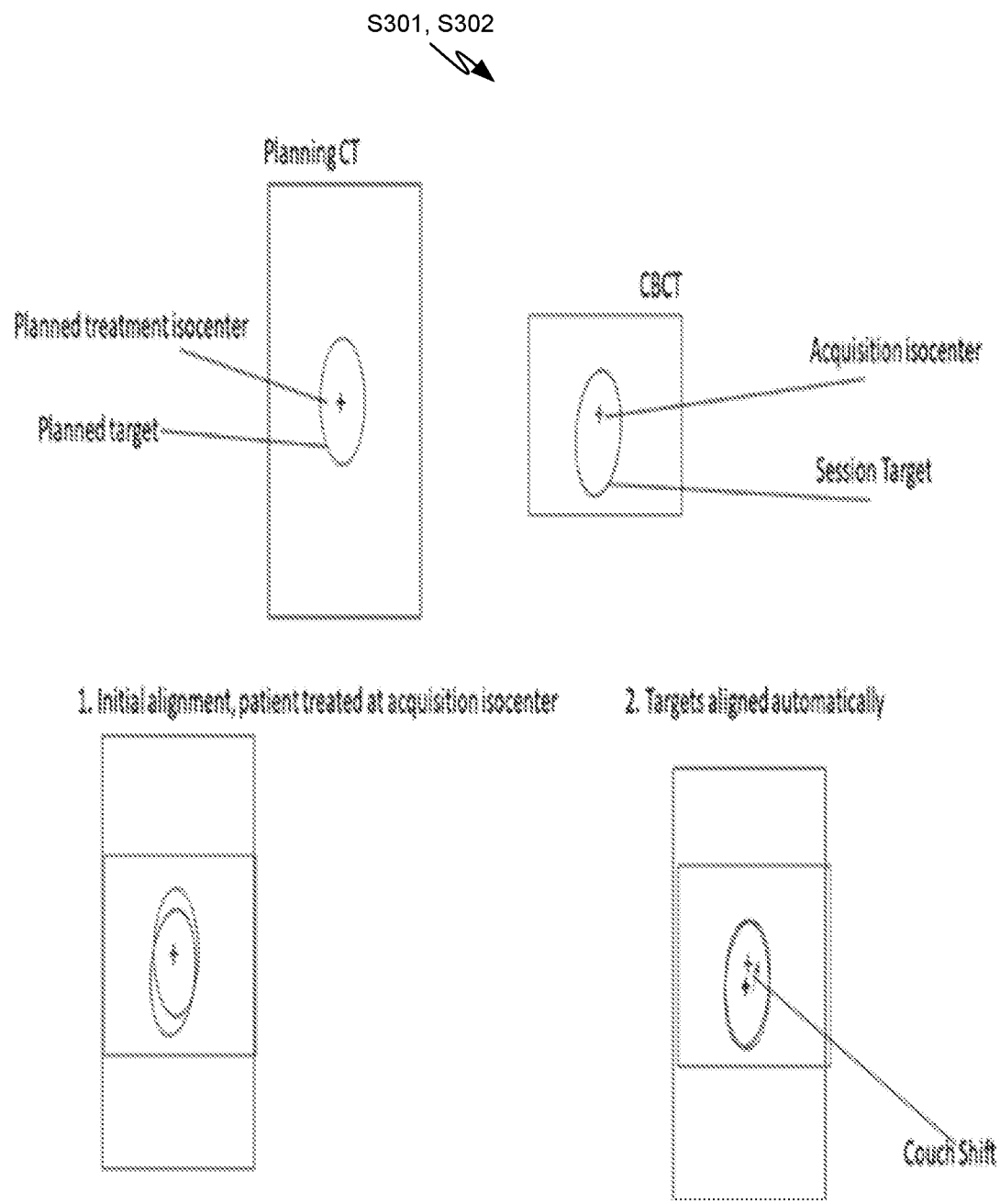
FIG. 8 is a process flow diagram for determining a treatment isocenter, according to various embodiments of the disclosed subject matter.
Figure 9:
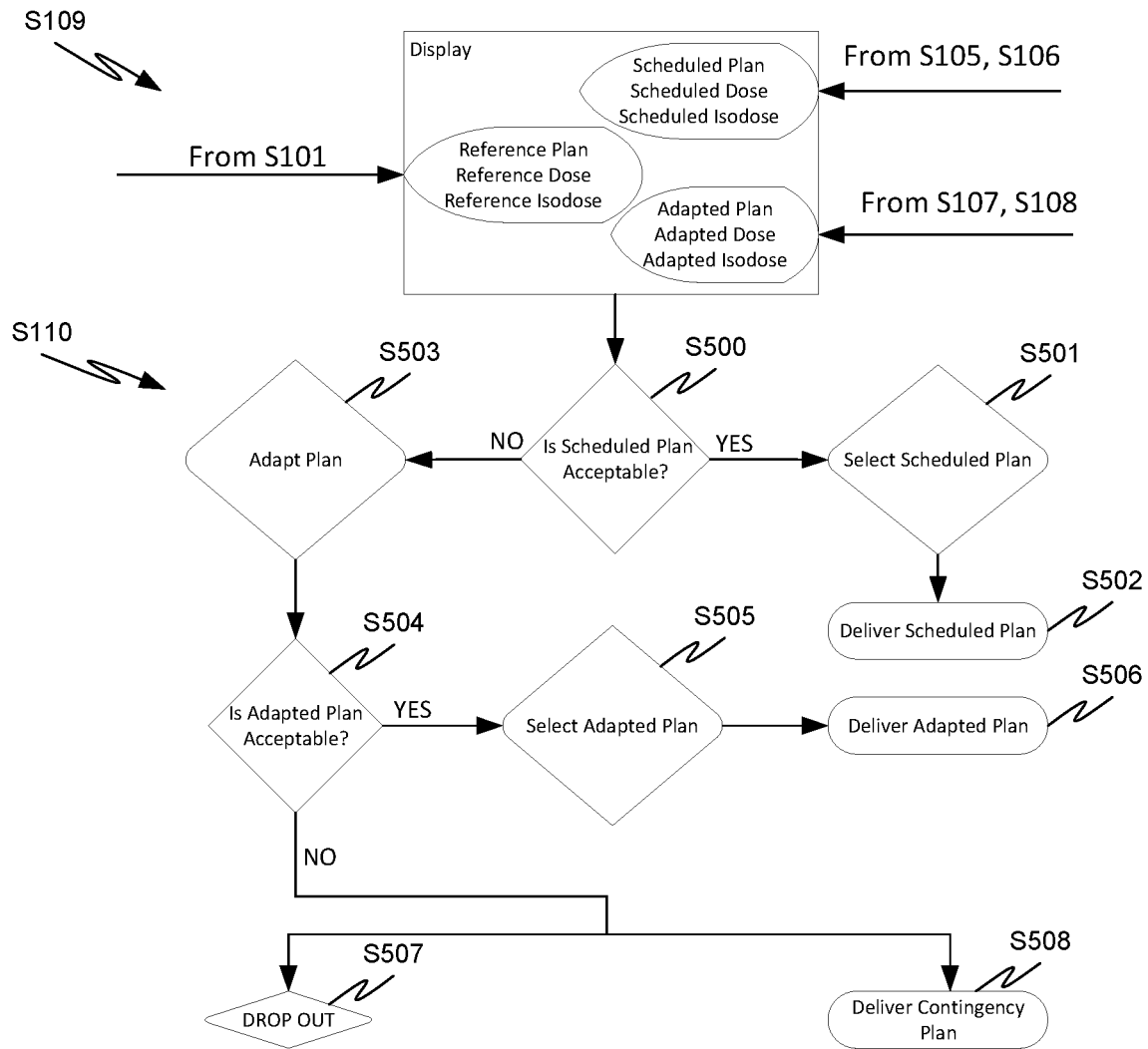
FIG. 9 is a process flow diagram for selecting a treatment plan, according to various embodiments of the disclosed subject matter.

Then, the RTT/MTA initializes the generation of contours of the reference structures on the treatment session image (Contouring, S104) to obtain a treatment session patient model. The details of this guided contouring process S104 are shown in FIGS. 5 and 6. The RTT/MTA then initializes the generation of different plans for the session patient model obtained in S104 and the selection of the appropriate plan (S105-S110) to be delivered to the patient (S111). In order to generate accurate treatment plans, however, an accurate session patient model needs to be generated. Namely, the target volumes (CTV, PTV, etc.), OARs, organs, anatomical structures, influencer structures, body outlines, etc. that were present in the reference image need to be correctly shown in the treatment session image, so that no further revisions/recontouring and no electron density map error corrections are needed to be made by a physician. The details of the plan generation and selection process (S105-S110) are shown in FIGS. 7-9. Optionally, the treatment delivery can be evaluated/monitored offline by a same or different physician.

Figure 3:
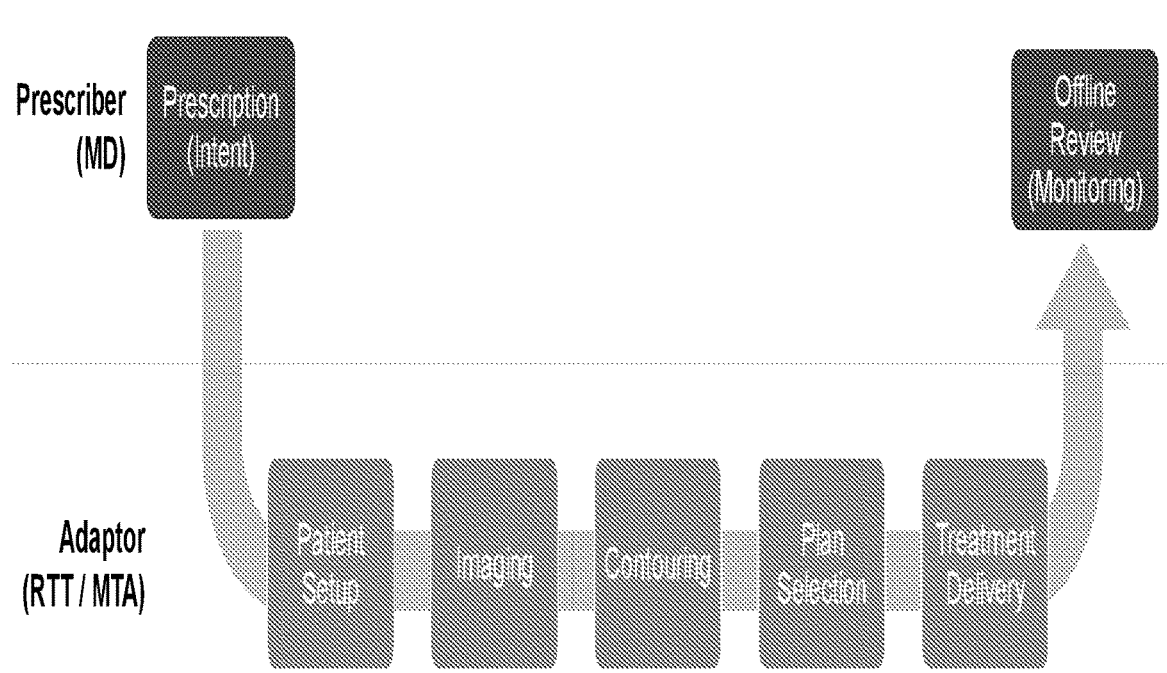
FIGS. 3-5 are workflow diagrams for use in on-couch adaptive radiation therapy, according to various embodiments of the disclosed subject matter.
Figure 4:
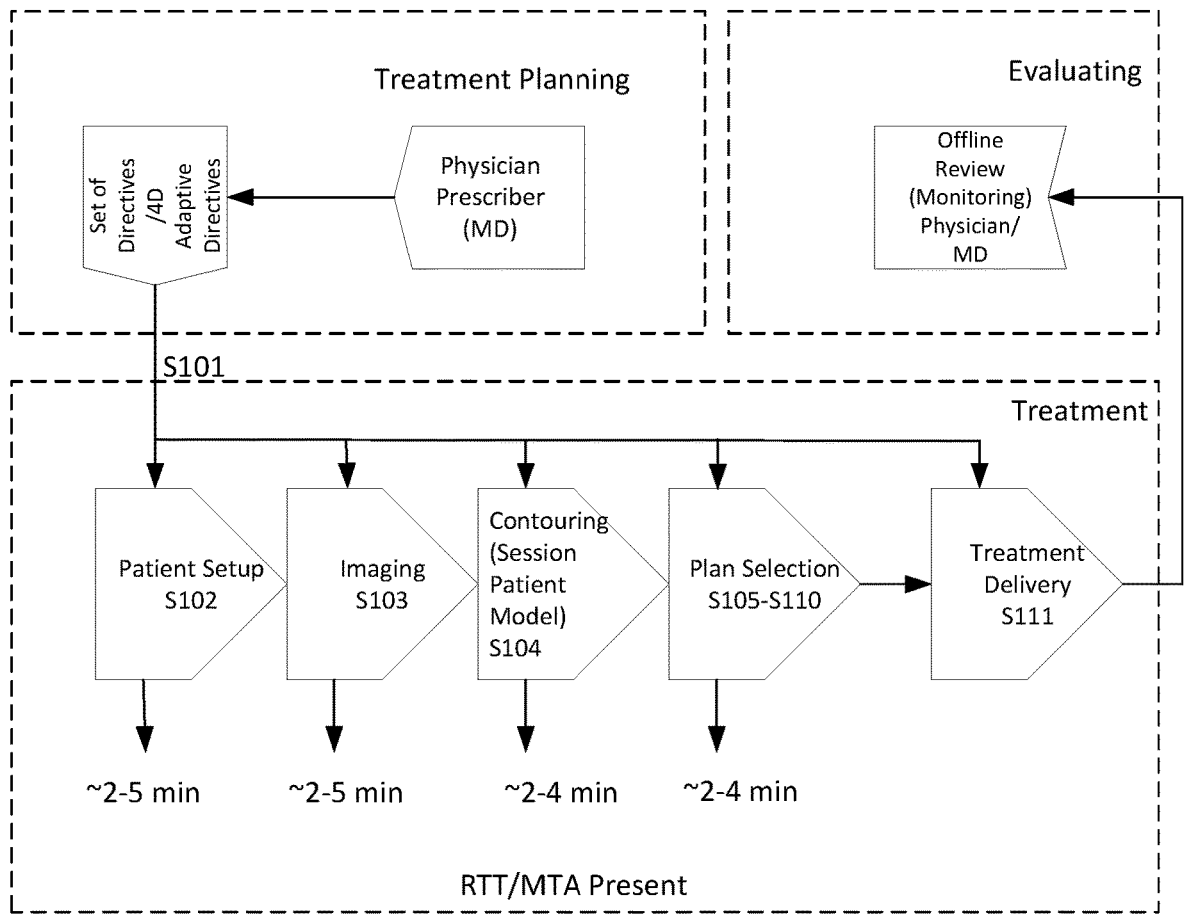
Figure 14:
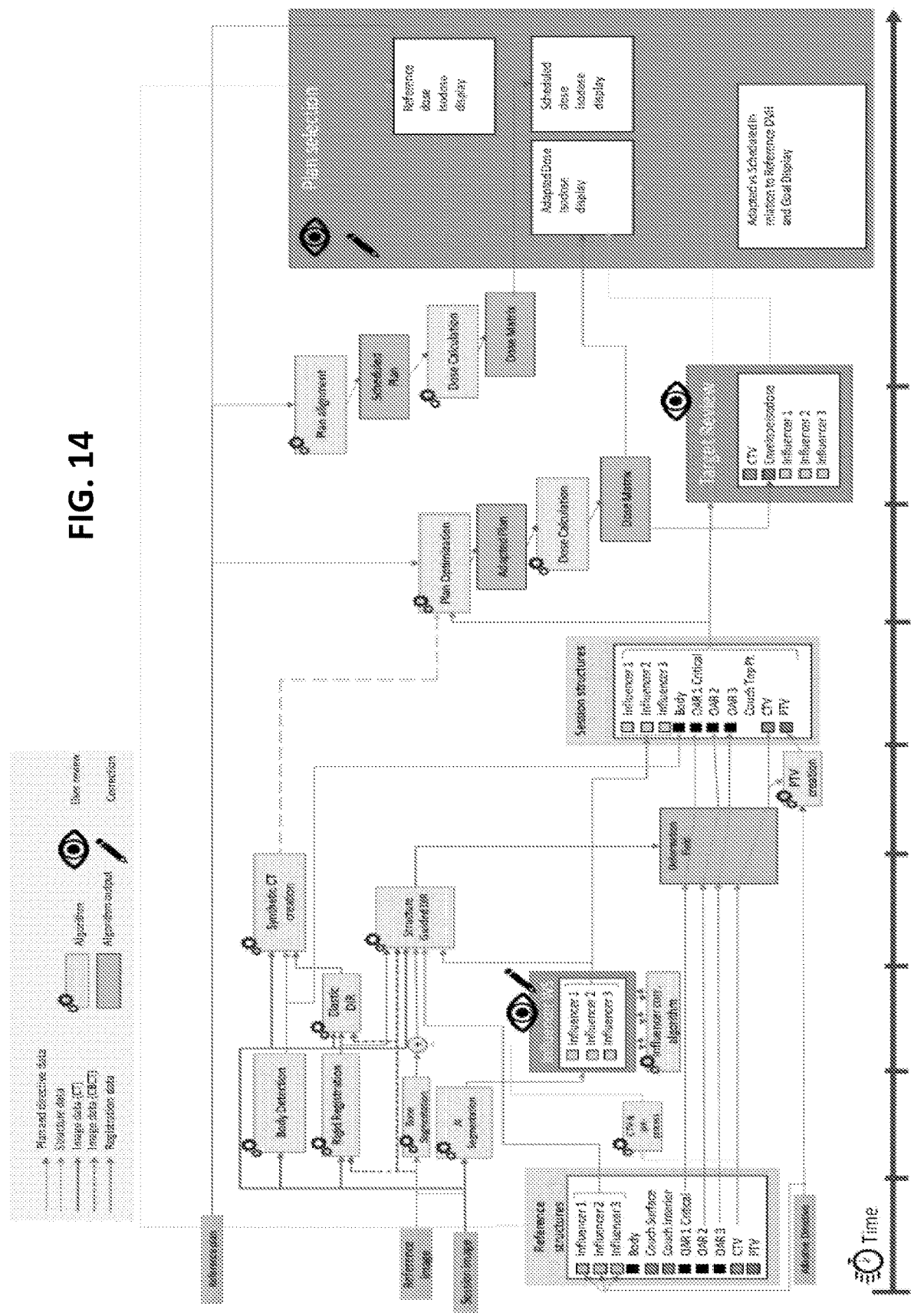
FIG. 14 is an on-couch adaptive workflow, according to various embodiments of the disclosed subject matter.

As shown in FIGS. 3-4, and 14, the on-couch adaptive workflow is guided by the set of directives made available in S101, so as to perform a series of automated steps by the RTT/MTA that allow for the generation of an accurate session patient model that need not be reviewed separately by a physician, and which can generate accurate treatment plans that the RTT/MTA can select from without additional physician input.

Contouring S104

As shown in FIG. 6, to generate a session patient model that accurately reflects the shape and location of the reference structures on the treatment session image, namely, a treatment session image including the contours of the structures that were present in the reference image (i.e., the reference structures), the session patient model is built in a step-wise fashion.

Step 1—Match Bones

Figure 15A:
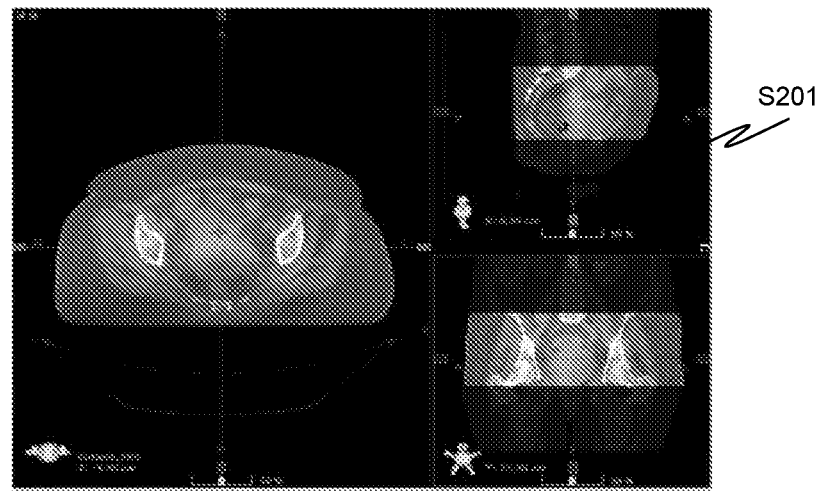
FIG. 15A illustrates a screen shot of an exemplary bone structure matching process, according to various embodiments of the disclosed subject matter.

As a first, optional step S200, the treatment session image obtained in step S103, which is an image that shows an anatomy of interest and may show one or more boney structures, is compared with the reference image which also includes a corresponding set of boney structures. For this, the RTT/MTA is provided on a console display with the reference image and the treatment session image as shown in FIG. 15A for comparison and analysis. If the RTT/MTA decides that the boney structures in the two images do not match (S201), the RTT/MTA initiates treatment couch adjustment in S202 to correct the positional error found by registering the two images. When the boney structures match, the RTT/MTA initiates the generation of the influencer structures on the treatment session image in S203. Alternatively, this step S200 could be performed in the background, without displaying information to the RTT/MTA. Alternatively, this step S200 could be performed after Step 3 described below.

Step 2—Generate and Evaluate Influencer Structures

Figure 10:
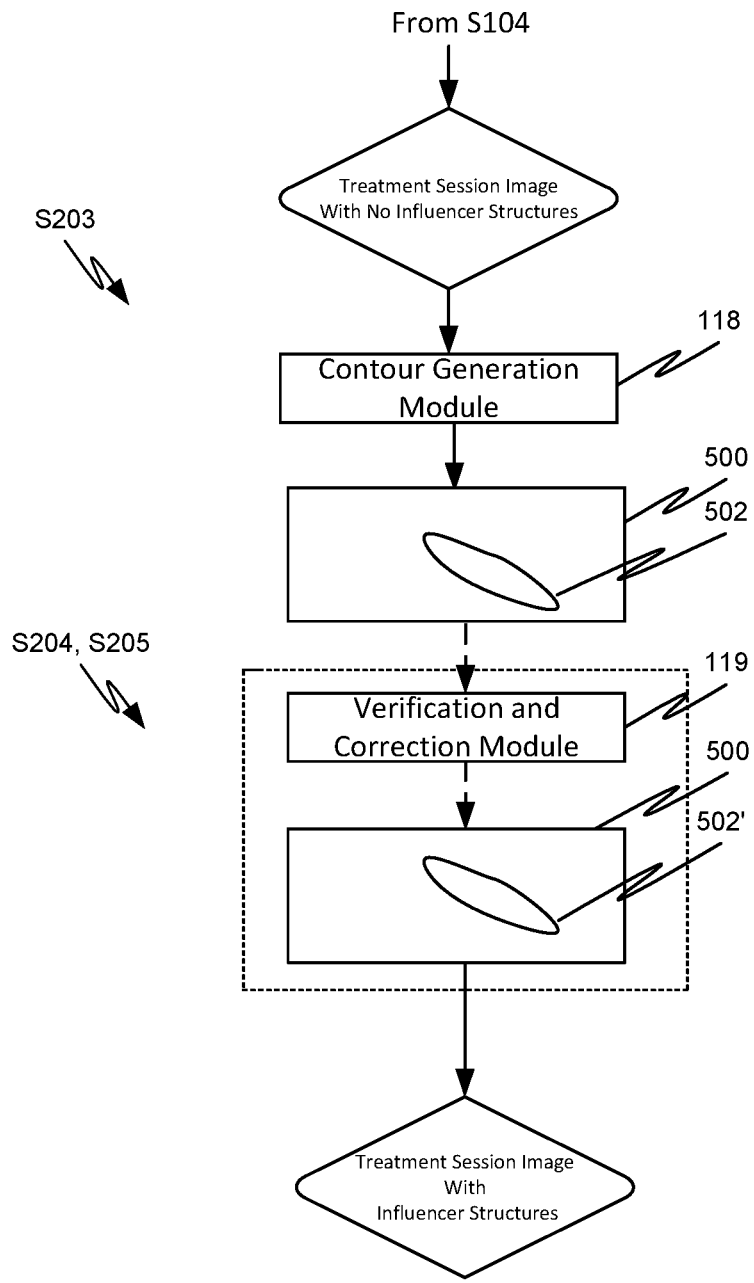
FIG. 10 is a process flow diagram for generating influencer structures on a treatment session image, according to various embodiments of the disclosed subject matter.

The generation of the influencer structures (S203) on the treatment session image obtained in S103 is shown in FIG. 10. As shown in FIG. 10, a treatment session image 500 obtained from the Imaging step S103 does not contain any delineations. Using the list of influencer structures that are included in the set of adaptive directives and which list is available to the RTT/MTA, the RTT/MTA initiates, via options made available to the RTT/MTA on the console, one of an automatic, manual, or a combination of automatic and manual delineation of the influencer structures in the list of influencer structures that are appropriate for the treatment site. For example, if the patient is treated for cervix uteri cancer, the influencer structures to be picked from the list of influencer structures for delineation are the bladder, the rectum and the uterus. Further, if other non-volumetric influencer structures were present in the reference image, these influencer structures are also delineated in the treatment session image 500.

As shown in FIG. 10, when initiated by the RTT/MTA, the selected influencer structures can be automatically delineated using various available automatic segmentation software (algorithms) executed by the contour generation module 118, that automatically detect the influencer structures and draw the respective contours 502. The influencer structures can also be created from the treatment session image data directly using artificial intelligence (AI) based segmentation, image analysis, shape models, etc. The influencer structures can also be derived from the previously segmented reference image via deformable or rigid image registration. The delineation can also be done manually by the RTT/MTA via an interactive graphical interface (GUI) for example, that allows the user to identify and draw the contours 502 on the treatment session image 500.

Once the contours 502 of the influencer structures are drawn on the treatment session image 500, the contours 502 may be further reviewed by the RTT/MTA using various available contour verification tools present in the verification module 119 of the GUI, for example (S204). Using the GUI, the user can modify, delete, redraw the automatically generated contours 502 (S205), to establish consistency between the influencer structures in the reference image and the influencer structures in the treatment session image 500.

Figure 11:
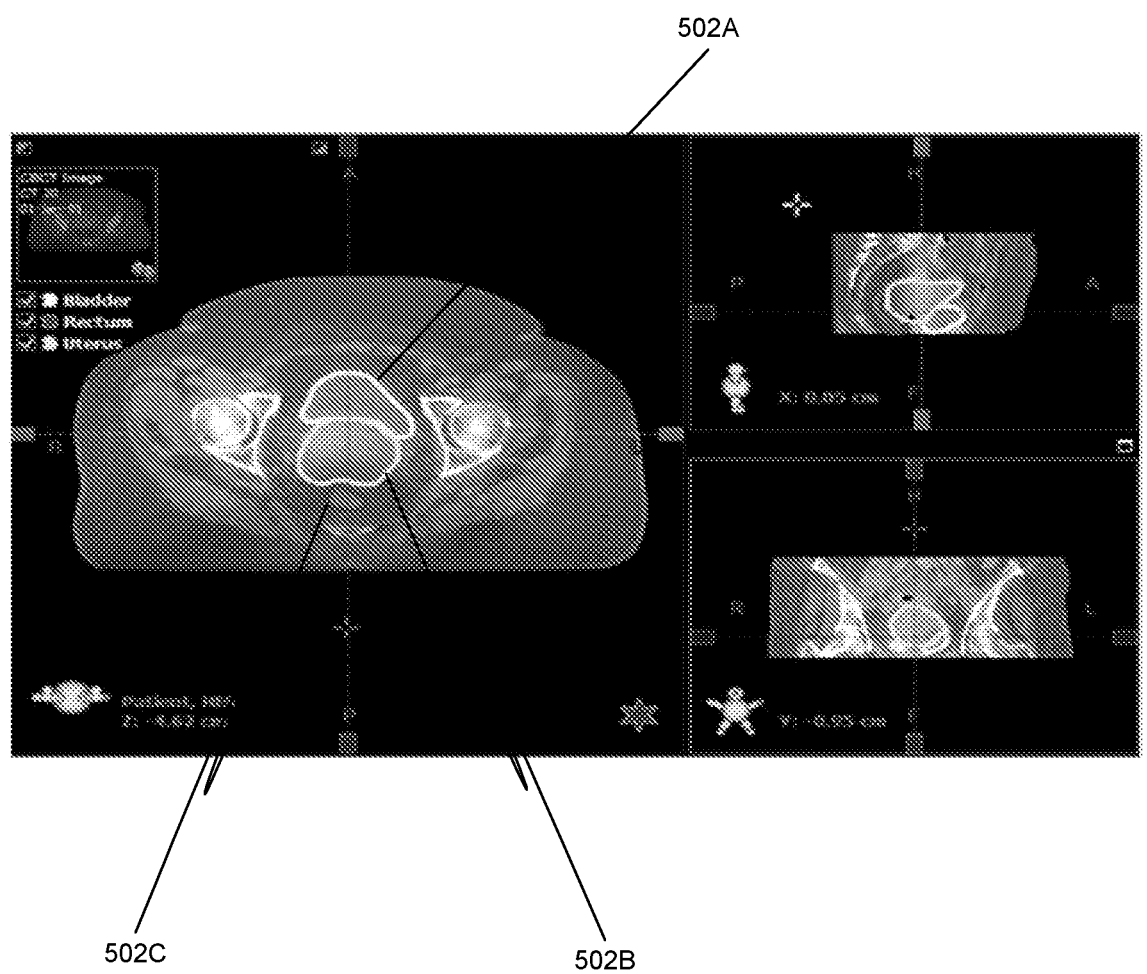
FIG. 11 illustrates a screen shot of an exemplary contour verification process display.

An exemplary verification process is shown in FIG. 11, where the contours for the bladder 502A, the uterus 502B, and the rectum 502C are reviewed from different views on a display device of a GUI. The verification module 119 may also support the user identifying locations where a correction to the influencer structures may be necessary (i.e., Sanity checks). The verification module 119 may also support the user verifying the correctness of the influencer structures by displaying a reference, such as the reference image, an anatomy atlas, contouring guidelines, etc.

Since the influencer structures deform significantly, the location of the influencer structures on the treatment session image 500 may be different from the location of the same influencer structures in the reference image 400, as shown in FIG. 17A.

Once the influencer structures are corrected (502'), if needed, by the RTT/MTA and the RTT/MTA determines that the patient anatomy of each influencer structure is captured correctly on the treatment session image 500, the RTT/MTA initiates the propagation of the rest of the reference structures (except the influencer structures) included in the reference image (S206). Namely, the RTT/MTA initiates propagation of the target volumes (CTV, PTV, etc.), OARs, and other anatomical structures of interest besides the influencer structures that were present in the reference image 400 (i.e., propagation of selective reference structures).

Step 3—Propagate and Evaluate Structures

Figure 12:
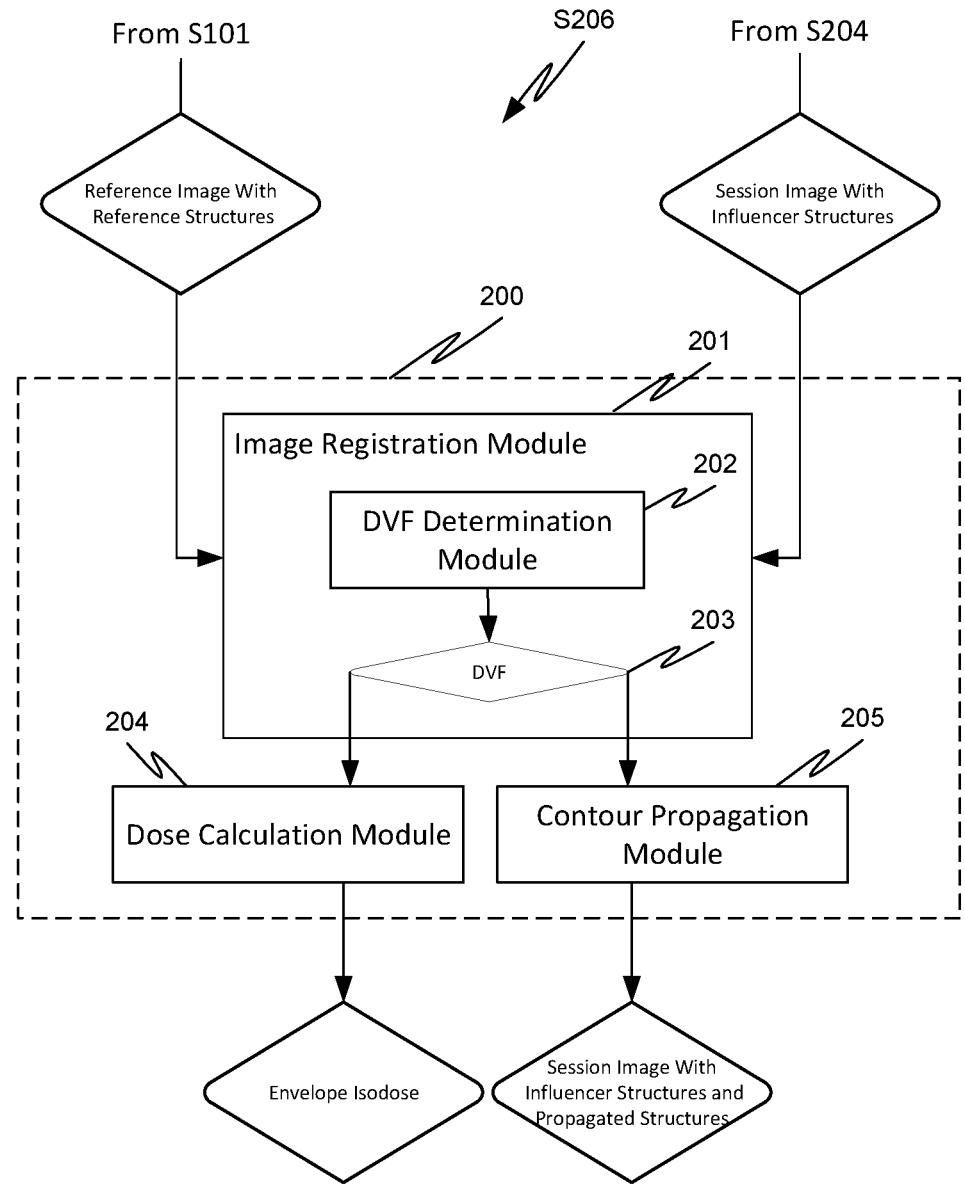
FIG. 12 is a process flow diagram for image registration and DVF generation, according to various embodiments of the disclosed subject matter.

The propagation is done using a structure-guided deformable registration algorithm (Structure-Guided DIR) that registers the image data of the reference image 400 with the image data of the treatment session image 500, and which generates, as a result, one or more deformable vector fields (DVFs) 203 using a DVF determination module 202 (see FIG. 12). The DVF 203 can then be used to propagate the target volumes (CTV, PTV, etc.), OARs, and other anatomical structures of interest from the reference image 400 to the treatment session image 500 using a contour propagation module 205.

The guided deformable registration is a deformable registration that is guided by the relationship between the influencer structures that are present in the reference image 400 and those that were generated in the treatment session image 500. The structure-guided deformable registration is a registration process wherein the influencer structures are used as inputs into a deformable registration algorithm to guide the deformation process, wherein the guiding is realized by incorporating a constraint in the deformable registration algorithm to enable matching of influencer structures present in the reference image with the same influencer structures generated in a subsequent treatment image. By applying the structure-guided deformable registration between the two images, the structure-guided deformable registration algorithm enables obtaining one or more deformation vector fields (DVFs) and, using the one or more deformation vector fields (DVFs), to accurately propagate selected reference structures from the reference image to the treatment session image. An exemplary structure-guided deformable registration process that can be applied to propagate the reference structures is disclosed in detail in U.S. patent application Ser. No. 16/144,253.

The one or more deformable vector fields (DVFs) 203 can also be used for dose accumulation determination by the dose calculation module 204 and to calculate the envelope isodose for the propagated structures. The controller 116 then initiates the contouring of the propagated structures (i.e., OARs, CTV, PTV) based on the propagated image data.

Figure 13:
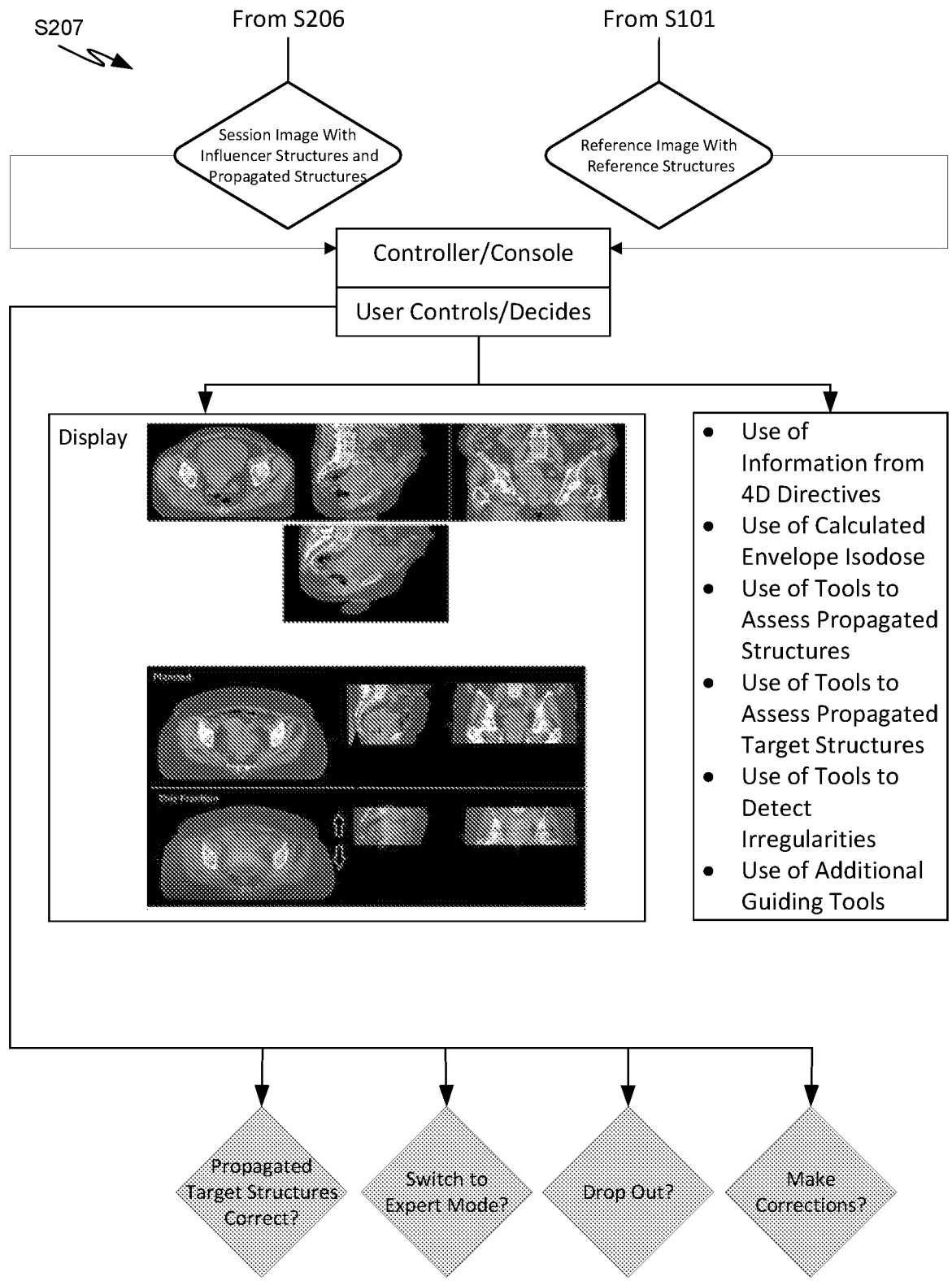
FIG. 13 is a process flow diagram for propagated session structure evaluation, according to various embodiments of the disclosed subject matter.
Figure 15B:
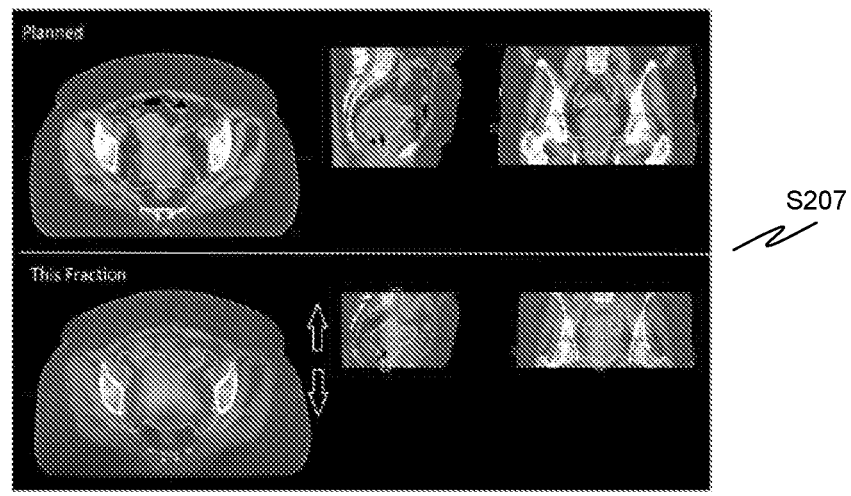
FIG. 15B illustrates a screen shot of an exemplary propagated target volume verification process, according to various embodiments of the disclosed subject matter.

Once the selective reference structures (target volumes, OARs, etc.) are propagated in S206, the RTT/MTA is prompted to evaluate one or more of the propagated structures in S207 shown in FIG. 13. In order to do that, the RTT/MTA is presented with the session treatment image 500 containing the generated influencer structures as well as the propagated structures (i.e., the contours of the session structures overlaid on the treatment session image) alongside the reference image 400 containing the reference structures (i.e., the contours of the reference structures overlaid on the reference image) on the console display, as shown in FIG. 15B. Optionally, overlaid on the two images are body outlines, as well as a radiation dose representation (Isodose lines, color washes, etc.).

The RTT/MTA utilizes the presented information to verify that the created target volumes, namely, the target volumes propagated to the treatment session image 500, represent the correct anatomical regions of the patient. In other words, the RTT/MTA compares the treatment session image which now has the generated influencer structures and the propagated structures (i.e., the session structures) overlaid thereon with the reference image which has the reference structures overlaid thereon, and using information such as the shapes and positions of the reference structures on the reference image (i.e., the reference patient model) included in the set of adaptive directives, calculates the positions and shapes of the propagated target volumes on the treatment session image, and determines whether the propagated target volumes (CTV, PTV, GTV, etc.) represent the same anatomical regions of the patient as those represented by the reference structures in the reference image.

The system 101 supports the RTT/MTA with this assessment by allowing the RTT/MTA to synchronize the views of the two images, letting the RTT/MTA select which information is displayed in the views, providing tools (software, hardware), such as measurement tools and volume information tools, for example, to automatically assess the shapes, positions, and locations of the propagated target volumes (CTV, PTV, GTV, etc.) on the treatment session image, and letting the RTT/MTA select which tools to use.

Optionally, the RTT/MTA is also provided with tools (hardware, software) to assess the other propagated structures (OARs, body outlines, etc.) on the treatment session image.

Optionally, the RTT/MTA is also provided with tools (hardware, software) that automatically detects irregularities in the propagated structures.

Optionally, the RTT/MTA is also provided with tools that, automatically or otherwise, guide the RTR/MTA to the locations where the irregularities are detected.

Optionally, the RTT/MTA may also use radiation doses calculated using the radiation prescription in the set of adaptive directives obtained in S101 and an adapted patient model created based on the generated influencer structures in the treatment session image and the calculated positions and shapes of the propagated target volumes on the treatment session image.

Based on the result of the assessment of the propagated target volumes, the RTT/MTA is presented with several options. If the result of the assessment is that the propagated target volumes are correct, the RTT/MTA accepts the propagated target volumes, in which case, the generated and the propagated contours, namely, the contours of the generated influencer structures and the contours of the propagated structures (together the Session Structures) are accepted as being anatomically consistent with the initially defined contours of the reference structures in the reference image, but adapted to the locations of the current anatomies. The shape and locations of the contours of the session structures on the treatment session image are also determined.

If the result of the assessment is that the propagated target volumes are not correct, the RTT/MTA is presented with several options to choose from to move forward. One option is to drop out (S210), another option is to select an expert mode (S208). The expert mode S208 allows the RTT/MTA to either apply a contour correction algorithm built into the system to automatically correct the propagated contours (S209), or to call on an expert located onsite or offline to automatically or manually correct the propagated contours (S209). The RTT/MTA is also provided with the option to make on-the-fly corrections in the propagated contours, and/or use additional supporting images (PET, MRI) from the set of adaptive directives to help in the reviewing process.

Upon acceptance of the propagated target volumes as correctly showing the anatomies of the reference patient model, the contours of the session structures on the treatment session image are accepted as the session patient model.

Plan Selection S107-S110

Generate Scheduled Plan S105

Once accepted, the propagated target volumes of the session patient model can be used to generate a scheduled plan, as shown in FIGS. 7-8. The RTT/MTA through the console can initiate the scheduled plan generation.

Initially, when starting the adaptive workflow, the patient 110 is setup on the treatment couch 112 the same way as for a standard radiation therapy treatment. Therefore, after positioning the patient 110 on the treatment couch 112, the patient 110 is taken to the radiation therapy system 100 isocenter, using traditional skin marks indicating the location of the isocenter.

When the treatment session image (i.e., the CBCT image, for example) 500 is acquired in S103, the center of the treatment session image 500 corresponds to the acquisition isocenter. If the patient 110 is treated by aligning the acquisition isocenter with the system isocenter, the patient 110 will not be treated correctly, since, as shown in FIG. 8, the session target volume does not align with the reference target volume. In order to determine the correct treatment isocenter (S301), once the RTT/MTA accepts the propagated target volume (i.e., the session target volume) on the treatment session image 500 (step S207), the system 100 is prompted to automatically align (S300) the reference target volume of the reference patient model obtained from S101 to the session target volume of the session patient model obtained in S104.

As shown in FIG. 8, this alignment provides the difference between the acquisition isocenter and the reference treatment isocenter. From this difference, the translation (X, Y, Z) values, namely, by how much in the X, Y, and Z direction does the patient 110 need to be moved for the two isocenters to align, is calculated. The calculated translation values are then applied to the acquisition isocenter so that the treatment isocenter location is determined in S301. This treatment isocenter location is then provided in S302 to a dose volume calculation algorithm which, using the information regarding the reference plan from S101, generates a scheduled plan. The scheduled plan also contains information regarding the new treatment couch 112 location, which will be communicated to the treatment delivery system 101 if the scheduled plan is selected for treatment. When the scheduled treatment plan contains new treatment couch position, it forces the RTT/MTA to apply (move the treatment couch 112) to the new location.

Generate Scheduled Dose Matrix S106

The scheduled plan generated in S105 is next applied to a dose calculation algorithm in S303 to calculate in S106 the radiation dose to be applied to the session target volume according to the scheduled plan. The scheduled dose matrix so generated (S304) is then sent together with the generated scheduled plan and scheduled isodose values to a display device to be displayed for the RTT/MTA in S109.

Generate Adapted Plan S107

Once accepted in S207, the propagated target volumes together with the other propagated structures (OARs, etc.) (together the propagated session structures) of the session patient model can be used to generate an adapted plan, as shown in FIGS. 5 and 7. The RTT/MTA through the console can initiate the adapted plan generation.

To generate the adapted plan, the propagated session structures together with a synthetic image of the patient (i.e., synthetic CT, for example) obtained in S103' are used as inputs to an automated plan generation algorithm in S400. The plan generation algorithm combines several components from existing components (Photon Optimization algorithm (PO-GPU) for VMAT and IMRT, SmartLMC algorithm for leaf sequencing, RapidPlan for DVH-estimation, FTDC-GPU for optimization dose calculation, AcurosXP-GPU for final dose calculation), and additionally, to support the automated adaptive workflow, further includes an additional component that allows for the automatic generation, automatic selection, and automatic continuous modification of optimization parameters by which the algorithm S401 and ultimately the generated plan S402 are optimized. This relieves the RTT/MTA from having to himself/herself provide optimization specific parameters (objectives, optimization structures, options, normal tissue handling, etc.) on a case by case basis. This not only reduces the time needed for the plan generation but also reduces potential errors that could be introduced by the RTT/MTA picking the wrong parameters.

To generate the synthetic CT, the treatment session image generated in S103 is further registered with the reference image including the reference structures obtained from S101. The image registration can include one or more of a rigid registration and elastic deformable registration (elastic DIR), and/or one or more of an atlas-based segmentation, bone segmentation, etc. The result of the rigid registration between the two images is used as an input to an elastic deformable registration algorithm (elastic DIR), and the registration data output from the elastic DIR together with the data regarding the detected body outlines from the treatment session image of S103 are used as inputs to a synthetic CT generation algorithm, as shown in FIG. 14.

The automated plan generation algorithm of S400 takes the created synthetic CT and the propagated session structures as inputs to modify the reference plan based on the new anatomy. The original treatment instruction, namely, the physician defined set of clinical goals contained in the set of adaptive directives in S101, are used in S401 to automatically generate a set of optimization parameters/criteria for the adaptive plan generation. The plan generation algorithm uses the automatically generated and selected optimization parameters to generate a plan in S402. The so generated plan in S402 is further automatically optimized using additional information, including reference plan optimization parameters, associated with the reference plan, which are included in the set of directives obtained in S101. The reference plan is used in S402 with the aim of optimizing the generated plan to a dose distribution of similar dosimetric characteristics as the dose distribution of the reference plan.

The information regarding the reference plan parameters used to optimize the generated plan in S402 also include radiation treatment system 100 delivery characteristics such as beam angles and monitor units, for example. These optimization parameters are used so as to obtain a new plan, namely, an adapted plan, which meets the original clinical goals to a similar degree as the original treatment plan.

Generate Adapted Dose Matrix S108

The adapted plan generated in S107 is next applied to a dose calculation algorithm in S403 to calculate in S108 the radiation dose to be applied to the session target volume according to the adapted plan. The adapted dose matrix so generated (S404) is then sent together with the generated adapted plan and adapted isodose values to the display device to be displayed for the RTT/MTA in S109.

Both the scheduled and the adapted plans can also be checked and validated before treatment delivery. Plan checks can be validated to ensure delivery on the treatment device using DICOM artifacts (reference plan, images, structures, doses, etc.), which are provided for independent quality assurance. Optionally the independent validation application communicates back to the adaptive workflow application with the results of the validation (QA).

Plan Display and Selection S109-S110

The scheduled plan together with the calculated scheduled dose matrix as well as the adapted plan together with the calculated adapted dose matrix are displayed for the RTT/MTA for selection, as shown in FIGS. 5 and 9. The RTT/MTA is also provided with one or more tools (hardware, software, etc.) to evaluate the scheduled plan and the adapted plan. The tools may include tools that provide Isodose distribution of the reference plan on the reference image, Isodose distribution of the scheduled plan on the treatment session image, Isodose distribution of the adapted plan on the session treatment image, Dose Volume Histograms (DVHs) of the reference plan, the scheduled plan and the adapted plan. The tools may also include tools for clinical goals evaluation to provide the reference clinical goal values, and the scheduled and adapted plan clinical actual values. Optionally, the RTT/MTA may be presented with other images, such as multi modal images (PET, MRI), that may help in the plan selection process. The RTT/MTA can select what information to be displayed on display S109 and what additional tools to use to help in the selection of the most appropriate plan.

Equipped with these tools and choices, the RTT/MTA determines in S500 whether the scheduled plan is the acceptable plan for the current treatment session. If the scheduled plan is acceptable, the RTT/MTA selects in S501 to deliver the scheduled plan in S502 for treatment delivery in S111. If the RTT/MTA determines in S500 that the scheduled plan is not acceptable, the RTT/MTA selects the adapted plan in S503 for evaluation. If the RTT/MTA determines in S504 that the adapted plan is the appropriate plan for the current treatment session, then the RTT/MTA selects in S505 to deliver in S506 the adapted plan for treatment delivery in S111. If the RTT/MTA determines in S504 that the adapted plan is also not acceptable for the current treatment session, then the RTT/MTA can choose to drop out in S507 or to use a contingency plan in S508 for treatment delivery. The contingency plan is a plan that is created based on the reference plan but for previously calculated average target volume positions (average CTV position) that include greater dose margins than those calculated for the reference target volumes.

The RTT/MTA uses the reference clinical goals and reference clinical goal values in the set of directives obtained in S101 to quantitatively assess if the scheduled and/or the adapted plan is medically necessary for the treatment session of the day (i.e., the current treatment session). For this, the reference clinical goal values and the actual clinical values for the scheduled and adapted treatment plans are presented to the RTT/MTA on the display, and the RTT/MTA selects the treatment plan that provides the clinical values closest to the reference clinical goal values.

Once the user selects a treatment plan, the radiation treatment will proceed in S111 according to the selected plan. The prescribing physician (MD) which generated the original treatment plan, the adaptive directives, and the adaptive workflow, or any other qualified physician, can review and/or monitor the treatment delivery offline, as shown in FIG. 5.

It is thus apparent that the disclosed subject matter enables for the use of a set of directives to guide an adaptive workflow in order to generate a session patient model and to select an appropriate treatment plan for the treatment session, as shown in FIG. 14. The adaptive workflow comprises obtaining a set of directives, the directives including information relating to a planned treatment of a patient; using the set of directives to guide the adaptive workflow to generate a session patient model in a step-wise fashion starting with the most variable anatomy; using directives from the set of directives to continuously and automatically optimize a treatment plan generated for the session model thereby obtaining an adapted plan for the treatment session; using the generated session model to automatically transfer control points of the planned treatment thereby generating a scheduled plan for the treatment session; and using directives form the set of directives to allow a user to select the treatment plan appropriate for the treatment session.

It is thus also apparent that the disclosed subject matter also enables a system to perform the guided adaptive workflow as described herein.

It will be appreciated that the aspects of the disclosed subject matter can be implemented, fully or partially, in hardware, hardware programmed by software, software instruction stored on a computer readable medium (e.g., a non-transitory computer readable medium), or any combination of the above.

For example, components of the disclosed subject matter, including components such as a controller, process, or any other feature, can include, but are not limited to, a personal computer or workstation or other such computing system that includes a processor, microprocessor, microcontroller device, or is comprised of control logic including integrated circuits such as, for example, an application specific integrated circuit (ASIC).

Features discussed herein can be performed on a single or distributed processor (single and/or multi-core), by components distributed across multiple computers or systems, or by components co-located in a single processor or system. For example, aspects of the disclosed subject matter can be implemented via a programmed general purpose computer, an integrated circuit device, (e.g., ASIC), a digital signal processor (DSP), an electronic device programmed with microcode (e.g., a microprocessor or microcontroller), a hard-wired electronic or logic circuit, a programmable logic circuit (e.g., programmable logic device (PLD), programmable logic array (PLA), field-programmable gate array (FPGA), programmable array logic (PAL)), software stored on a computer-readable medium or signal, an optical computing device, a networked system of electronic and/or optical devices, a special purpose computing device, a semiconductor chip, a software module or object stored on a computer-readable medium or signal.

When implemented in software, functions may be stored on or transmitted over as one or more instructions or code on a computer-readable medium. The steps of a method or algorithm disclosed herein may be embodied in a processor-executable software module, which may reside on a computer-readable medium. Instructions can be compiled from source code instructions provided in accordance with a programming language. The sequence of programmed instructions and data associated therewith can be stored in a computer-readable medium (e.g., a non-transitory computer readable medium), such as a computer memory or storage device, which can be any suitable memory apparatus, such as, but not limited to read-only memory (ROM), programmable read-only memory (PROM), electrically erasable programmable read-only memory (EEPROM), random-access memory (RAM), flash memory, disk drive, etc.

As used herein, computer-readable media includes both computer storage media and communication media, including any medium that facilitates transfer of a computer program from one place to another. Thus, a storage media may be any available media that may be accessed by a computer. By way of example, and not limitation, such computer-readable media may comprise RAM, ROM, EEPROM, CD-ROM or other optical disk storage, magnetic disk storage or other magnetic storage devices, or any other medium that may be used to carry or store desired program code in the form of instructions or data structures and that may be accessed by a computer.

Also, any connection is properly termed a computer-readable medium. For example, if the software is transmitted from a website, server, or other remote source using a transmission medium (e.g., coaxial cable, fiber optic cable, twisted pair, digital subscriber line (DSL), or wireless technologies such as infrared, radio, and microwave), then the transmission medium is included in the definition of computer-readable medium. Moreover, the operations of a method or algorithm may reside as one of (or any combination of) or a set of codes and/or instructions on a machine readable medium and/or computer-readable medium, which may be incorporated into a computer program product.

One of ordinary skill in the art will readily appreciate that the above description is not exhaustive, and that aspects of the disclosed subject matter may be implemented other than as specifically disclosed above. Indeed, embodiments of the disclosed subject matter can be implemented in hardware and/or software using any known or later developed systems, structures, devices, and/or software by those of ordinary skill in the applicable art from the functional description provided herein.

In this application, unless specifically stated otherwise, the use of the singular includes the plural, and the separate use of "or" and "and" includes the other, i.e., "and/or." Furthermore, use of the terms "including" or "having," as well as other forms such as "includes," "included," "has," or "had," are intended to have the same effect as "comprising" and thus should not be understood as limiting.

Any range described herein will be understood to include the endpoints and all values between the endpoints. Whenever "substantially," "approximately," "essentially," "near," or similar language is used in combination with a specific value, variations up to and including 10% of that value are intended, unless explicitly stated otherwise.

The terms "system," "device," and "module" have been used interchangeably herein, and the use of one term in the description of an embodiment does not preclude the application of the other terms to that embodiment or any other embodiment.

Many alternatives, modifications, and variations are enabled by the present disclosure. While specific examples have been shown and described in detail to illustrate the application of the principles of the present invention, it will be understood that the invention may be embodied otherwise without departing from such principles. For example, disclosed features may be combined, rearranged, omitted, etc. to produce additional embodiments, while certain disclosed features may sometimes be used to advantage without a corresponding use of other features. Accordingly, Applicant intends to embrace all such alternative, modifications, equivalents, and variations that are within the spirit and scope of the present invention.

The invention claimed is:

1. A method for radiation treatment, comprising:
positioning a patient on a treatment couch of a radiation treatment system and moving the patient to an imaging position;
acquiring one or more treatment session images of the patient by irradiating the patient with radiation beams;
applying a series of automated steps guided by a set of previously determined directives including information representing a planned treatment for the patient to generate a treatment session patient model;
generating a plurality of treatment plans based on the generated treatment session patient model;
selecting an appropriate treatment plan from the plurality of generated treatment plans to be delivered to the patient; and
delivering the selected treatment plan onto the patient.

2. The method of claim 1, wherein the set of directives includes information regarding planned radiation dose, planned clinical goals, planned clinical goal values, reference patient model, reference treatment plan, list of influencer structures, and one or more reference images.

3. The method of claim 2, wherein the applying of the series of automated steps includes:
generating a treatment session image of a portion of the patient, the treatment session image containing an anatomy of interest;
generating one or more influencer structures from the list of influencer structures on the treatment session image;
evaluating the generated influencer structures based on one or more directives of the set of directives;
propagating target structures of a reference image to the treatment session image upon acceptance of the generated influencer structures;
evaluating the propagated target structures based on one or more directives of the set of directives; and
upon acceptance of the propagated target structures, accepting the treatment session image including the influencer structures and the propagated target structures as the session patient model.

4. The method of claim 3, wherein
the target structures include:
a first set of target structures representing contours of a primary tumor; and a second set of target structures representing contours of one or more primarily affected organs (OARs), and the influencer structures include:
  a first set of influencer structures representing contours of one or more organs that affect one or more of a shape, size or location of one or more of the target structures; and
  a second set of influencer structures representing contours of non-volumetric structures.

5. The method of claim 4, wherein the generating of the one or more influencer structures includes applying one of a manual, automatic, or a combination of manual and automatic segmentation, or by propagating the one or more influencer structures from the reference image to the treatment session image by deformable and/or rigid deformation.

6. The method of claim 5, wherein the propagating of the target structures includes propagating from the reference image to the treatment session image using structure-guided deformable registration, wherein the structure-guided deformable registration is deformable registration that is guided by one or more of the influencer structures.

7. The method of claim 3, wherein the evaluating, accepting, and selecting is done by a single user.

8. The method of claim 7, wherein the determining whether the one or more influencer structures are acceptable includes:
  presenting, to the user, the treatment session image including the generated influencer structures and the reference image including corresponding reference influencer structures for comparison; and
  the user verifying that the generated influencer structures correspond to the reference influencer structures.

9. The method of claim 8, further including displaying contouring/segmentation guidelines to the user to be used for the verifying.

10. The method of claim 9, wherein the determining whether the propagated target structures are acceptable includes:
  presenting, to the user, the treatment session image including the propagated target structures and the reference image including corresponding reference target structures for comparison; and
  the user verifying that the propagated first set of target structures on the treatment session image represent same anatomical regions of the patient as the reference first set of target structures in the reference image.

11. The method of claim 10, wherein the determining further includes one or more of:
  synchronizing the reference image with the treatment session image prior to the verifying;
  using information relating to shapes and positions of the propagated and reference first set of target structures in the treatment session image and the reference image;
  using information relating to radiation dose representations in the reference image and the treatment session images;
  using automated tools to detect irregularities in the compared first set of target structures; and
  using automated tools to guide the user to locations where irregularities are detected.

12. The method of claim 11, further comprising allowing the user to select to correct the propagated first set of target structures or to default to another user for correction upon a determination that the propagated first set of target structures are not acceptable.

13. The method of claim 12, wherein the generating of a first treatment plan for the session patient model, includes:
  obtaining a reference isocenter location for the reference patient model from the set of directives;
  determining an acquisition isocenter location for the session patient model;
  aligning the accepted propagated first set of target structures in the session patient model with the corresponding reference first set of target structures in the reference patient model;
  determining a difference between the location of the reference isocenter and the location of the acquisition isocenter;
  determining a treatment session isocenter location by applying the determined difference to the acquisition isocenter location; and
  using the treatment session isocenter location as an input to a plan generation algorithm to generate the first treatment plan.

14. The method of claim 13, wherein the generating of a second treatment plan includes:
  generating a synthetic image for the patient by registering the treatment session image with the reference image;
  using the synthetic image and the propagated target structures as input to a treatment plan generation algorithm to generate a treatment plan, wherein the plan generation algorithm includes optimization parameters which are automatically generated based on the planned clinical goals included in the set of directives; and
  generating the second treatment plan by optimizing the generated plan using information relating to the reference treatment plan included in the set of directives,
  wherein the optimization parameters are automatically modified and automatically selected without the user's input.

15. The method of claim 14, wherein the selecting of the appropriate treatment plan includes:
  evaluating whether the first treatment plan is acceptable for the current treatment session using the clinical goals from the set of directives;
  selecting the second treatment plan when determined that the first treatment plan is not acceptable;
  evaluating whether the second treatment plan is acceptable; and
  selecting a contingency plan when determined that the second treatment plan is not acceptable.

16. The method of claim 15, wherein the selecting of the appropriate treatment session further includes:
  presenting, to the user, the first and second treatment plans in a comparison view;
  illustrating isodose distribution of the reference plan on the reference patient model, isodose distribution of the first treatment plan on the treatment session model, and isodose distribution of the second treatment plan on the treatment session model;
  illustrating dose volume histograms of the reference plan, the first treatment plan and the second treatment plan;
  presenting the planned clinical goal values;
  presenting actual clinical values for the first and second treatment plans; and
  selecting the treatment plan that provides the clinical values closest to the planned clinical goal values,
  wherein the determining further includes selecting, by the user, a contingency plan when neither the first and second treatment plans achieve the planned clinical goals.

17. The method of claim 3, further comprising evaluating, using a reference image from the set of directives, the reference image containing a reference bone structure, the treatment session image being accepted when a bone structure of interest in the treatment session image matches the bone structure in the reference image.

18. A radiation treatment system, comprising:
a treatment couch configured to support a patient;
a radiation source to irradiate the patient with radiation beams;
an imaging device configured to generate treatment session images of the patient;
a computer processing system configured to:
obtain a set of directives, the set of directives including information representing a planned treatment for the patient;
apply a series of automated steps guided by the set of directives to generate a treatment session patient model;
generate a plurality of treatment plans based on the generated treatment session patient model; and
allow a user to select an appropriate treatment plan from the plurality of generated treatment plans to be delivered to the patient; and
a controller configured to deliver the selected treatment plan onto the patient.

19. The system of claim 18,
wherein the set of directives includes information regarding planned radiation dose, planned clinical goals, planned clinical goal values, reference patient model, reference treatment plan, list of influencer structures, and one or more reference images; and
the applying of the series of automated steps includes:
generating a treatment session image of a portion of the patient, the treatment session image containing an anatomy of interest;
generating one or more influencer structures from the list of influencer structures on the treatment session image;
evaluating the generated influencer structures based on one or more directives of the set of directives;
propagating target structures of a reference image to the treatment session image upon acceptance of the generated influencer structures;
evaluating the propagated target structures based on one or more directives of the set of directives; and
upon acceptance of the propagated target structures, accepting the treatment session image including the influencer structures and the propagated target structures as the session patient model,
the target structures including:
a first set of target structures representing contours of a primary tumor; and
a second set of target structures representing contours of one or more primarily affected organs (OARs), and
the influencer structures including:
a first set of influencer structures representing contours of one or more organs that affect one or more of a shape, size or location of one or more of the target structures; and
a second set of influencer structures representing contours of non-volumetric structures.

20. The system of claim 19, wherein the generating of the plurality of treatment plans includes generating a first treatment plan and a second treatment plan,
the generating of the first treatment plan including:
obtaining a reference isocenter location for the reference patient model from the set of directives;
determining an acquisition isocenter location for the session patient model;
aligning the accepted propagated first set of target structures in the session patient model with the corresponding reference first set of target structures in the reference patient model;
determining a difference between the location of the reference isocenter and the location of the acquisition isocenter;
determining a treatment session isocenter location by applying the determined difference to the acquisition isocenter location; and
using the treatment session isocenter location as an input to a plan generation algorithm to generate a first treatment plan; and
the generating of the second treatment plan including:
generating a synthetic image for the patient by registering the treatment session image with the reference image;
using the synthetic image and the propagated target structures as input to a treatment plan generation algorithm to generate a treatment plan, wherein the plan generation algorithm includes optimization parameters which are automatically generated based on the planned clinical goals included in the set of directives; and
generating a second treatment plan by optimizing the generated plan using information relating to the reference treatment plan included in the set of directives, wherein the optimization parameters are automatically modified and automatically selected without the user's input.

* * * * *